(12) United States Patent
Liao et al.

(10) Patent No.: US 10,221,239 B2
(45) Date of Patent: Mar. 5, 2019

(54) TRPM4 CHANNEL INHIBITORS FOR STROKE TREATMENT

(71) Applicant: Singapore Health Services Pte Ltd, Singapore (SG)

(72) Inventors: Ping Liao, Singapore (SG); Kok Poh Loh, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 103 days.

(21) Appl. No.: 14/392,213

(22) PCT Filed: Jun. 30, 2014

(86) PCT No.: PCT/SG2014/000314
§ 371 (c)(1),
(2) Date: Dec. 23, 2015

(87) PCT Pub. No.: WO2014/209239
PCT Pub. Date: Dec. 31, 2014

(65) Prior Publication Data
US 2016/0168245 A1 Jun. 16, 2016

(30) Foreign Application Priority Data
Jun. 28, 2013 (SG) ................ 201305129-7

(51) Int. Cl.
| C07K 16/00 | (2006.01) |
| C07K 16/28 | (2006.01) |
| C12N 15/113 | (2010.01) |
| A61K 31/713 | (2006.01) |
| A61K 39/395 | (2006.01) |
| A61K 45/06 | (2006.01) |
| A61K 39/00 | (2006.01) |

(52) U.S. Cl.
CPC ........... *C07K 16/28* (2013.01); *A61K 31/713* (2013.01); *A61K 39/3955* (2013.01); *A61K 45/06* (2013.01); *C12N 15/1138* (2013.01); *A61K 2039/505* (2013.01); *C07K 2317/24* (2013.01); *C07K 2317/34* (2013.01); *C07K 2317/74* (2013.01); *C07K 2317/76* (2013.01); *C07K 2317/77* (2013.01); *C12N 2310/14* (2013.01)

(58) Field of Classification Search
None
See application file for complete search history.

(56) References Cited

U.S. PATENT DOCUMENTS

2010/0092469 A1* 4/2010 Simard .................. A61K 31/56
514/1.1
2014/0378548 A1* 12/2014 Friese .................... A61K 45/06
514/593

FOREIGN PATENT DOCUMENTS

| WO | WO 2008/089103 | 7/2008 |
| WO | WO 2008/098160 | 8/2008 |
| WO | WO 2009/002832 A2 | 12/2008 |
| WO | WO 2010/033560 A2 | 3/2010 |
| WO | WO 2014/209239 | 6/2014 |

OTHER PUBLICATIONS

Wu, Nie, Huse, and Watkins. Humanization of a murine monoclonal antibody by simultaneous optimization of framework and CDR residues. Journal of Molecular Biology, 1999. vol. 294, pp. 151-162.*
Skolnick and Fetrow. From genes to protein structure and function: novel applications of computational approaches in the genomic era. Trends in Biotechnology, 2000. vol. 18, pp. 34-39.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Paul, Fundamental Immunology, 3rd edition, 1993, pp. 292-295.*
Bendig (1995) Methods: a companion methods in enzymology 8: 83-93.*
MacCallum et al. (1996) J. Mol. Biol. 262: 732-745.*
Astrup, Jens, Bo K. Siesjö, and Lindsay Symon. "Thresholds in cerebral ischemia—the ischemic penumbra." Stroke 12.6 (1981): 723-725.
Becerra, Alvaro, et al. "Transient receptor potential melastatin 4 inhibition prevents lipopolysaccharide-induced endothelial cell death." Cardiovascular research (2011): cvr135.
Chandrashekran, Anil, et al. "Lentiviral vector transduction of spermatozoa as a tool for the study of early development." *FEBS open bio* 4.1 (2014): 266-275.
Cianfriglia, Maurizio, et al. "Simple immunization protocol for high frequency production of soluble antigen-specific hybridomas." *Hybridoma* 2.4 (1983): 451-457.
Cole, Susan PC, et al. "A strategy for the production of human monoclonal antibodies reactive with lung tumor cell lines," *Cancer research* 44.7 (1984): 2750-2753.
De Meyer, Simon F., et al. "von Willebrand factor an emerging target in stroke therapy." *Stroke* 43.2 (2012): 599-606.
Favilla, Christopher G., et al. "Sulfonylurea use before stroke does not influence outcome." *Stroke* 42.3 (2011): 710-715.

(Continued)

Primary Examiner — Michael D Pak
(74) Attorney, Agent, or Firm — Lisa M. Warren, Esq.; Morse, Barnes-Brown & Pendleton, P.C.

(57) ABSTRACT

The present invention relates to methods for treating ischemic stroke including extension of the therapeutic time window for reperfusion. More particularly, the invention relates to a method of treating stroke in a subject by inhibiting the transient receptor potential melastatin 4 (TRPM4) channel. The present invention also provides uses of TRPM4 inhibitors, TRPM4 antibodies and kits for use in the methods of the invention.

6 Claims, 22 Drawing Sheets
Specification includes a Sequence Listing.

(56) References Cited

OTHER PUBLICATIONS

Gerzanich, Volodymyr, et al. "De novo expression of Trpm4 initiates secondary hemorrhage in spinal cord injury." Nature medicine 15.2 (2009): 185-191.

Grand, Teddy, et al. "9-Phenanthrol inhibits human TRPM4 but not TRPM5 cationic channels." British journal of pharmacology 153.8 (2008): 1697-1705.

Kahle, Kristopher T., et al. "Molecular mechanisms of ischemic cerebral edema: role of electroneutral ion transport." *Physiology* 24.4 (2009): 257-265.

Karagiannis, Panagiotis, et al. "Characterisation of an engineered trastuzumab IgE antibody and effector cell mechanisms targeting HER2/neu-positive tumour cells." *Cancer immunology, immunotherapy* 58.6 (2009): 915-930.

Köhler, Georges, and Cesar Milstein. "Continuous cultures of fused cells secreting antibody of predefined specificity." nature 256 (1975): 495-497.

Kozbor, Danuta, and John C. Roder. "The production of monoclonal antibodies from human lymphocytes." *Immunology Today* 4.3 (1983): 72-79.

Kruse, Martin, et al. "Impaired endocytosis of the ion channel TRPM4 is associated with human progressive familial heart block type I." *The Journal of clinical investigation* 119.9 (2009): 2737-2744.

Kunte, Hagen, et al. "Hemorrhagic transformation of ischemic stroke in diabetics on sulfonylureas." *Annals of neurology* 72.5 (2012): 799-806.

Liao, Ping, et al. "Smooth muscle-selective alternatively spliced exon generates functional variation in Cav1.2 calcium channels." Journal of Biological Chemistry 279.48 (2004): 50329-50335.

Morrison, Sherie L., et al. "Chimeric human antibody molecules: mouse antigen-binding domains with human constant region domains." *Proceedings of the National Academy of Sciences* 81.21 (1984): 6851-6855.

Neuberger, Michael S., Gareth T. Williams, and Robert O. Fox. "Recombinant antibodies possessing novel effector functions." *Nature* 312.5995 (Dec. 1984): 604-608.

Nilius, Bernd, et al. "Voltage dependence of the Ca2+-activated cation channel TRPM4." Journal of Biological Chemistry 278.33 (2003): 30813-30820.

Nilius, Bernd, et al. "The selectivity filter of the cation channel TRPM4." *Journal of Biological Chemistry* 280.24 (2005): 22899-22906.

Nilius, Bernd, et al. "Transient receptor potential cation channels in disease." *Physiological reviews* 87.1 (2007): 165-217.

Reading, Stacey A., and Joseph E. Brayden. "Central role of TRPM4 channels in cerebral blood flow regulation." *Stroke* 38.8 (2007): 2322-2328.

Riechmann, Lutz, et al. "Reshaping human antibodies for therapy." Nature 332.6162 (1988): 323-327.

Sala-Rabanal, Monica, Shizhen Wang, and Colin G. Nichols. "On potential interactions between non-selective cation channel TRPM4 and sulfonylurea receptor SUR1." Journal of Biological Chemistry 287.12 (2012): 8746-8756.

Schattling, Benjamin, et al. "TRPM4 cation channel mediates axonal and neuronal degeneration in experimental autoimmune encephalomyelitis and multiple sclerosis." Nature medicine 18.12 (2012): 1805-1811.

Simard, J. Marc, et al. "Newly expressed SUR1-regulated NCCa-ATP channel mediates cerebral edema after ischemic stroke." *Nature medicine* 12.4 (2006): 433-440.

Marc Simard, J., Kristopher T. Kahle, and Volodymyr Gerzanich. "Molecular mechanisms of microvascular failure in central nervous system injury—synergistic roles of NKCC1 and SUR1/TRPM4: A review," Journal of neurosurgery 113.3 (2010): 622-629.

Takeda, Shun-ichi, et al. "Construction of chimaeric processed immunoglobulin genes containing mouse variable and human constant region sequences." *Nature* 314.6010 (1984): 452-454.

Vennekens, Rudi, et al. "Increased IgE-dependent mast cell activation and anaphylactic responses in mice lacking the calcium-activated nonselective cation channel TRPM4." *Nature immunology* 8.3 (2007): 312-320.

Vennekens, R., and B. Nilius. "Insights into TRPM4 function, regulation and physiological role." Transient Receptor Potential (TRP) Channels. Springer Berlin Heidelberg, 2007. 269-285.

Verhoeyen, Cesar Milstein, "Reshaping human antibodies: grafting an antilysozyme activity." *Science,* New Series, vol. 239, No. 4847, (1988).

Walcott, Brian P., Kristopher T. Kahle, and J. Marc Simard. "Novel treatment targets for cerebral edema." Neurotherapeutics 9.1 (2012): 65-72.

Woo, Seung Kyoon, et al. "The sulfonylurea receptor 1 (Sur1)-transient receptor potential melastatin 4 (Trpm4) channel." Journal of Biological Chemistry 288.5 (2013): 3655-3667.

Yu, Chye Yun, Gandi Ng, and Ping Liao. "Therapeutic antibodies in stroke." Translational stroke research 4.5 (2013): 477-483.

Zhao, Heng, et al. "Akt contributes to neuroprotection by hypothermia against cerebral ischemia in rats." *The Journal of neuroscience* 25.42 (2005): 9794-9806.=.

Simard, J. Marc, Kirill V. Tarasov, and Volodymyr Gerzanich. "Non-selective cation channels, transient receptor potential channels and ischemic stroke." *Biochimica et Biophysica Acta (BBA)— Molecular Basis of Disease* 1772.8 (2007): 947-957.

International Search Report for International Application No. PCT/SG2014/000314, dated Aug. 19, 2014.

\* cited by examiner

FIGURE 1

Rat TRPM4 protein sequence (NCBI Accession # NP_001129701 XP_574447)

```
   1 MVGQEKEQSW IPKIFRKKVC TTFIVDLHDD AGGTLCQCGQ PRDAHPSVAV EDAFGAAVVT
  61 EWNSDEHTTE KPTDAYGDLD FTYSGRKSSN FLRLSDRTDP ATVYSLVTRS WGFRAPNLVV
 121 SVLGGSEGPV LQTWLQDLLR RGLVRAAQST GAWIVTGGLH TGIGRHVGVA VRDHQTASTG
 181 GSKVVAMGVA PWGVVRNRDM LINPKGSFPA RYRWRGDPED GVEFPLDYNY SAFFLVDDGT
 241 YGRMGGENRF RLRFESYVAQ QKTGVGGTGI DIPVLLLLIE GDEKMLKRIE DATQAQLPCL
 301 LVAGSGGAAD CLVETLEDTL APGSGGLRRG EARDRIRRYF PKGDPEVLQA QVERIMTRKE
 361 LLTVYSSEDG SEEFETIVLR ALVKACGSSE ASAYLDELRL AVAWNRVDIA QSELFRGDIQ
 421 WRSFHLEASL MDALLNDRPE FVRLLISHGL SLGHFLTPVR LAQLYSAVSP NSLIRNLLDQ
 481 ASHASSSKSP PANGAAELRP PNVGQVLRTL LGETCAPRYP ARNTRHSLLG QDHRENDSLL
 541 MDWANMQQDA SFEQAPWSDL LIWALLLNRA QMAIYFWEKG SNSVASALGA CLLLRVMARL
 601 EWEAEEAARP KDLAAKFESM SVDLFGECYH NSEYRAARLL LRRCPLWGEA TCIQLAMQAD
 661 ARAFFAQDGV QSLLTQKWWG EMDSTNPIWA LLLTFFCPPL IYTNLILFRK SEEEPTQKDL
 721 DFDMDSSMNG AGPLGPAEPS AKVALERRRR RRPGHTLCCG GCSKRWSYFW GAPVTAFLGN
 781 VVSYLLFLLL FAHVLLVDFQ PTKPGVFELL LYFWAFTLLC EELRQGLGGG WGTLANGGPG
 841 PGKAPLRHPL HLYLLDTWNQ CDLLALTCFL LGVGCRLTPG LFDLGRTVLC LDFMIFTLRL
 901 LHIFTVNKQL GPKIVIVSKM MKDVFFFLFF LCVWLVAYGV ATEGILRPQD RSLPSILRRV
 961 FYRPYLQIFG QIPQEEMDVA LMNPSNCSAE RGSWAHPEGP VAGSCVSQYA NWLVVLLLIV
1021 FLLVANILLL NLLIAMFSYT FNKVHGNSDL YWKAQRYSLI REFHSRPALA PPLIIISHLR
1081 LLFKWLRRCH RTNLPASPVF EHFRVCLSKE AERTLLTWES VHKENFLLAQ ARDKRDSDSE
1141 RLKRTSQKVD TALKQLGQIR EYDRRLRGLE REVQHCSRVL TWMAEALSHS ALLPPGGPPP
1201 PSPTGSKD
```

FIGURE 2

Human (TRPM4b) Isoform 1

```
        10         20         30         40         50         60
MVVPEKEQSW IPKIFKKKTC TTFIVDSTDP GGTLCQCGRP RTAHPAVAME DAFGAAVVTV 70         80         90        100        110        120
WDSDAHTTEK PTDAYGELDF TGAGRKHSNF LRLSDRTDPA AVYSLVTRTW GFRAPNLVVS 130        140        150        160        170        180
VLGGSGGFVL QTWLQDLLRR GLVRAAQSTG AWIVTGGLHT GIGRHVGVAV RDHQMASTGG 190        200        210        220        230        240
TKVVAMGVAP WGVVRNRDTL INPKGSFPAR YRWRGDPEDG VQFFLDYNYS AFFLVDDGTH 250        260        270        280        290        300
GCLGGENRFR LRLESYISQQ KTGVGGTGID IPVLLLLIDG DEKMLTRIEN ATQAQLPCLL 310        320        330        340        350        360
VAGSGGAADC LAETLEDTLA PGSGGARQGE APDRIRRFFP KGDLEVLQAQ VERIMTRKEL 370        380        390        400        410        420
LTVYSSEDGS EEFETIVLKA LVKACGSSEA SAYLDELRLA VAWNRVDIAQ SELFRGDIQW 430        440        450        460        470        480
RSFHLEASLM DALLNDRPEF VRLLISHGLS LGHFLTPMRL AQLYSAAFSN SLIRNLLDQA 490        500        510        520        530        540
SHSAGTKAPA LKGGAAELRP PDVGHVLRML LGKMCAPRYP SGGAWDPHPG QGFGESMYLL 550        560        570        580        590        600
SDKATSPLSL DAGLGQAPWS DLLLWALLLN PAQMAMYFWE MGSNAVSSAL GACLLLRVMA 610        620        630        640        650        660
RLEPDAEEAA RRKDLAFKFE GMGVDLFGEC YRSSEVRAAP LLLRPCPLWG DATCLQLAMQ
```

```
         670        680        690        700        710        720
ADARAFFAQD GVQSLITQKW WGDMASTTPI WALVLAFFCP PLIYTRLITF RKSEEEPTRE 730        740        750        760        770        780
ELEFDMDSVI NGEGPVGTAD PAEKTPLGVP RQSGRPGCCG GRCGGPRCLP PWFHFWGAPV 790        800        810        820        830        840
TIFMGNVVSY LLFLLLFSRV LLVDFQPAPP GSLELLLYFW AFTLLCEELR QGLSGGGGSL 850        860        870        880        890        900
ASGGPGPGHA SLSQRLRLYL ADSWNQCDLV ALTCFLLGVG CPLTPGLYHL GRTVLCIDFM 910        920        930        940        950        960
VFTVRLLHIF TVNKQLGPKI VIVSKMMKDV FFFLFFLGVW LVAYGVATEG LLRPRDSDFP 970        980        990       1000       1010       1020
SILRRVFYRP YLQIFGQIPQ EDMDVALMEH SNCSSEPGFW AHPPGAQAGT CVSQYANWLV 1030       1040       1050       1060       1070       1080
VLLLVIFLLV ANILLVNLLI AMFSYTPGKV QGNSDLYWKA QRYRLIREFH SRPALAPPFI 1090       1100       1110       1120       1130       1140
VISHLRLLLR QLCRRPRSPQ PSSPALEHFR VYLSKEAERK LLTWESVHKE NFLLARARDK 1150       1160       1170       1180       1190       1200
RESDSERLKR TSQKVDLALK QLGHIREYEQ RLKVLEREVQ QCSRVLGWVA EALSPSALLP

1210
PGGPPPPDLP GSKD
```

CONTINUATION OF FIGURE 2

FIGURE 3

Mouse TRPM4 Isoform 1

```
         10         20         30         40         50         60
    MVGPEKEQSW IPRIFRKKVC TTFIVDLSDD AGGTLCQCGQ PRDAHPSVAV EDAFGAAVVT 70         80         90        100        110        120
    EWNSDEHTTE KPTDAYGDLD FTYSGRKHSN FLRLSDRTDP ATVYSLVTRS WGFRAPNLVV 130        140        150        160        170        180
    SVLGGSGGFV LQTWLQDLLR RGLVRAAQST GAWIVTGGLH TGIGRHVGVA VRDHQTASTG 190        200        210        220        230        240
    SSKVVAMGVA PWGVVRNRDM LINPKGSFPA RYRWRGDPED GVEFPLDYNY SAFFLVDDGT 250        260        270        280        290        300
    YGRLGGENRF RLRFESYVAQ QKTGVGGTGI DIPVLLLLID GDEKMLKRIE DATQAQLPCL 310        320        330        340        350        360
    LVAGSGGAAD CLVETLEDTL APGSGGLRRG EARDRIRRYF PKGDPEVLQA QVERIMTRKE 370        380        390        400        410        420
    LLTVYSSEDG SEEFETIVLR ALVKACGSSE ASAYLDELRL AVAWNRVDIA QSELFRGDIQ 430        440        450        460        470        480
    WRSFHLEASL MDALLNDRPE FVRLLISHGL SLGHFLTPVR LAQLYSAVSP NSLIRNLLDQ 490        500        510        520        530        540
    ASHASSSKSP PVNGTVELRP PNVGQVLRTL LGETCAPRYP ARNTRDSYLG QDHKENDSLL 550        560        570        580        590        600
    MDWANKQPST DASFEQAPWS DLLIWALLLN RAQMAIYFWE KGSNSVASAL GACLLLRVMA 610        620        630        640        650        660
    RLESEAEEAA RRKDLAATFE SMSVDLFGEC YHNSEERAAR LLLRRCPLWG EATCLQLAMQ
```

```
      670        680        690        700        710        720
ADARAFFAQD GVQSLLTQKW WGEMDSTTPI WALLLAFFCP PLIYTNLIVF RKSEEEPTQK 730        740        750        760        770        780
DLDFDMDSSI NGAGPPGTVE PSAKVALERR QRRRPGRALC CGKFSKRWSD FWGAPVTAFL 790        800        810        820        830        840
GNVVSYLLFL LLFAHVLLVD FQPTKPSVSE LLLYFWAFTL LCEELRQGLG GGWGSLASGG 850        860        870        880        890        900
RGPDRAPLRH RLHLYLSDTW NQCDLLALTC FLLGVGCRLT PGLFDLGRTV LCLDFMIFTL 910        920        930        940        950        960
RLLHIFTVNK QLGPKIVIVS KMMKDVFFFL FFLCVWLVAY GVATEGILRP QDRSLPSILR 970        980        990       1000       1010       1020
RVFYRPYLQI FGQIPQEEMD VALMIPGNCS MERGSWAHPE GPVAGSCVSQ YANWLVVLLL 1030       1040       1050       1060       1070       1080
IVFLLVANIL LLNLLIAMFS YTFSKVHGNS DLYWKAQRYS LIREFHSRPA LAPPLIIISH 1090       1100       1110       1120       1130       1140
VRLLIKWLRR CRRCRRANLP ASPVFEHFRV CLSKEAERKL LTWESVHKEN FLLAQARDKR 1150       1160       1170       1180       1190       1200
DSDSERLKRT SQKVDTALKQ LGQIREYDRR LRGLEREVQH CSRVLTWMAE ALSHSALLPP

1210
GAPPPPSPTG SKD
```

CONTINUATION OF FIGURE 3

FIGURE 5
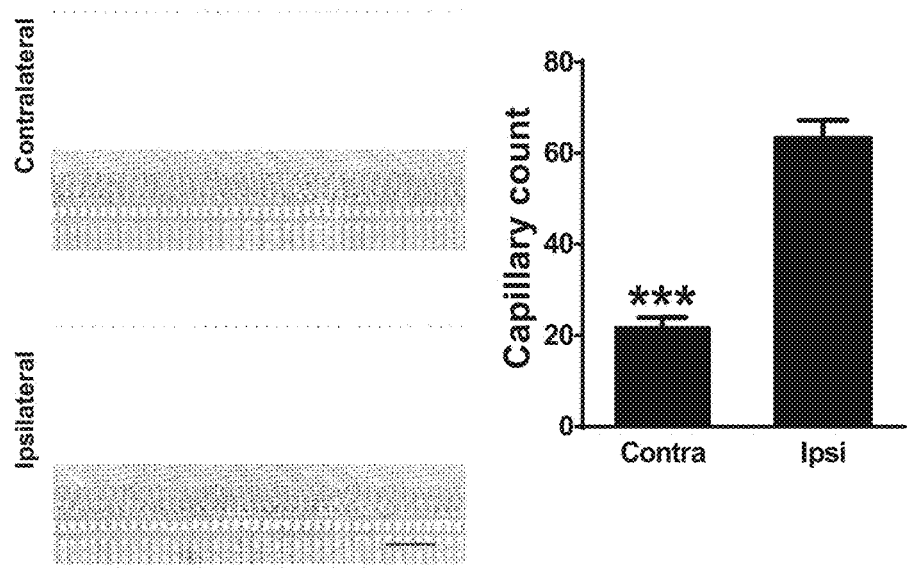
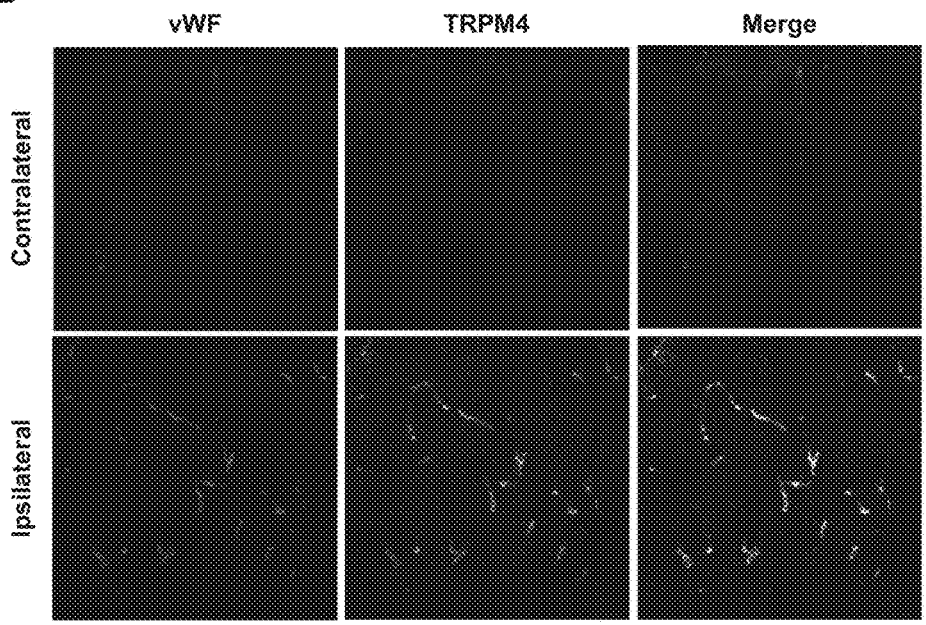

FIGURE 6
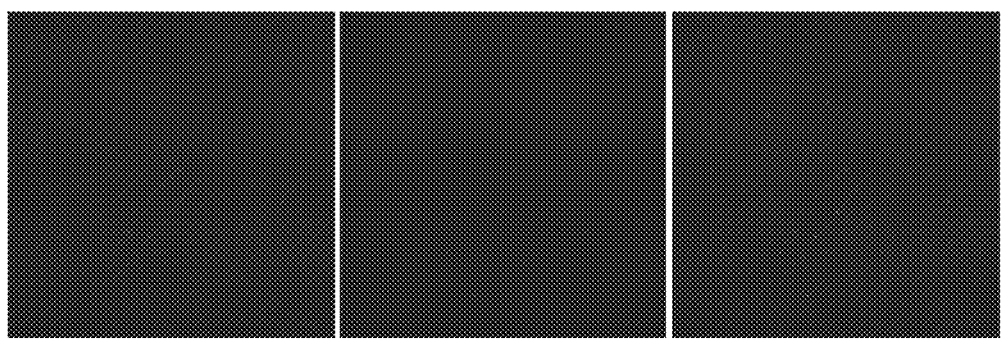
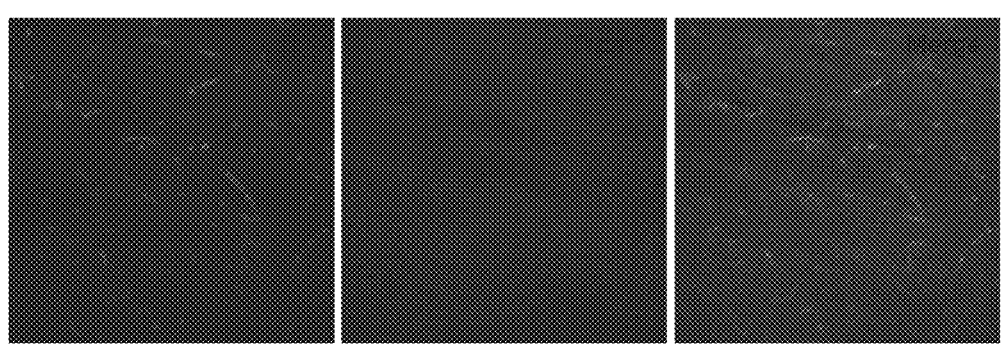

CONTINUATION OF FIGURE 8
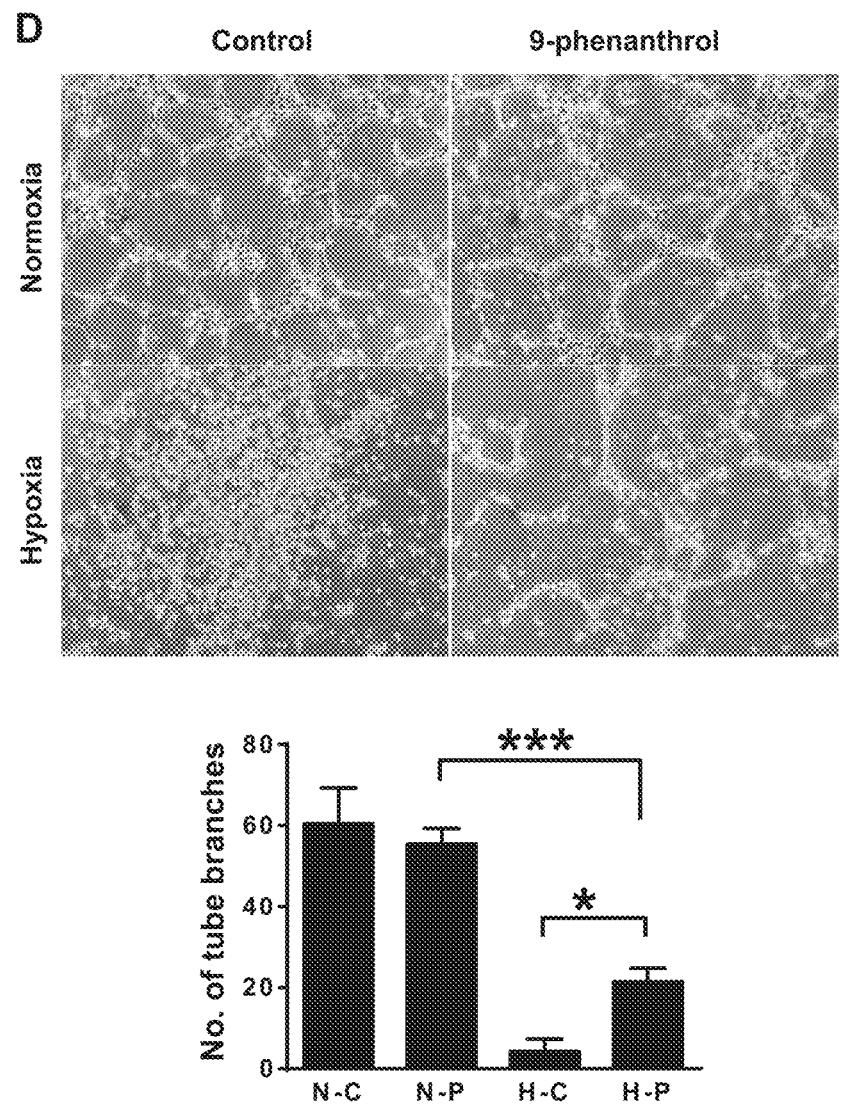

FIGURE 9
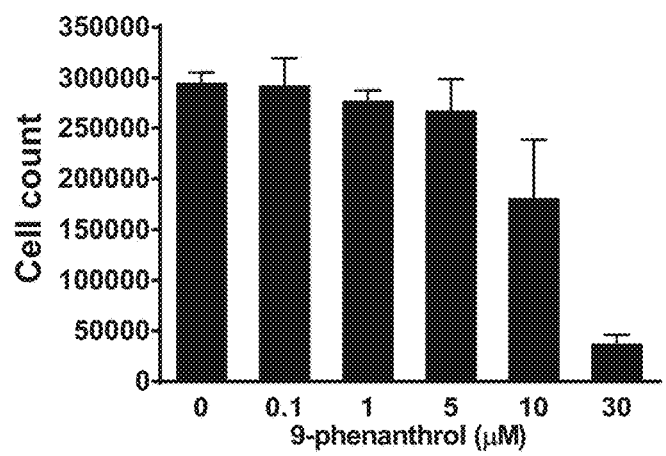
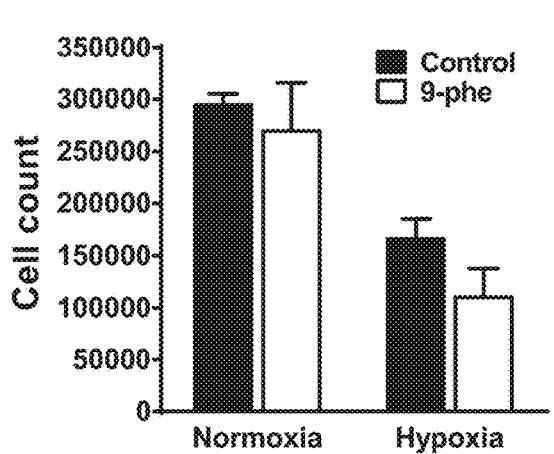
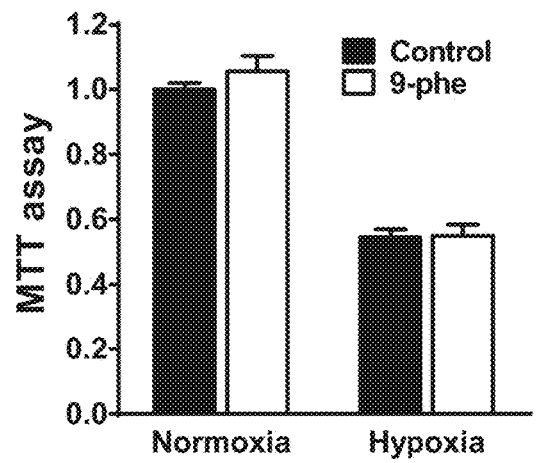

CONTINUATION OF FIGURE 10
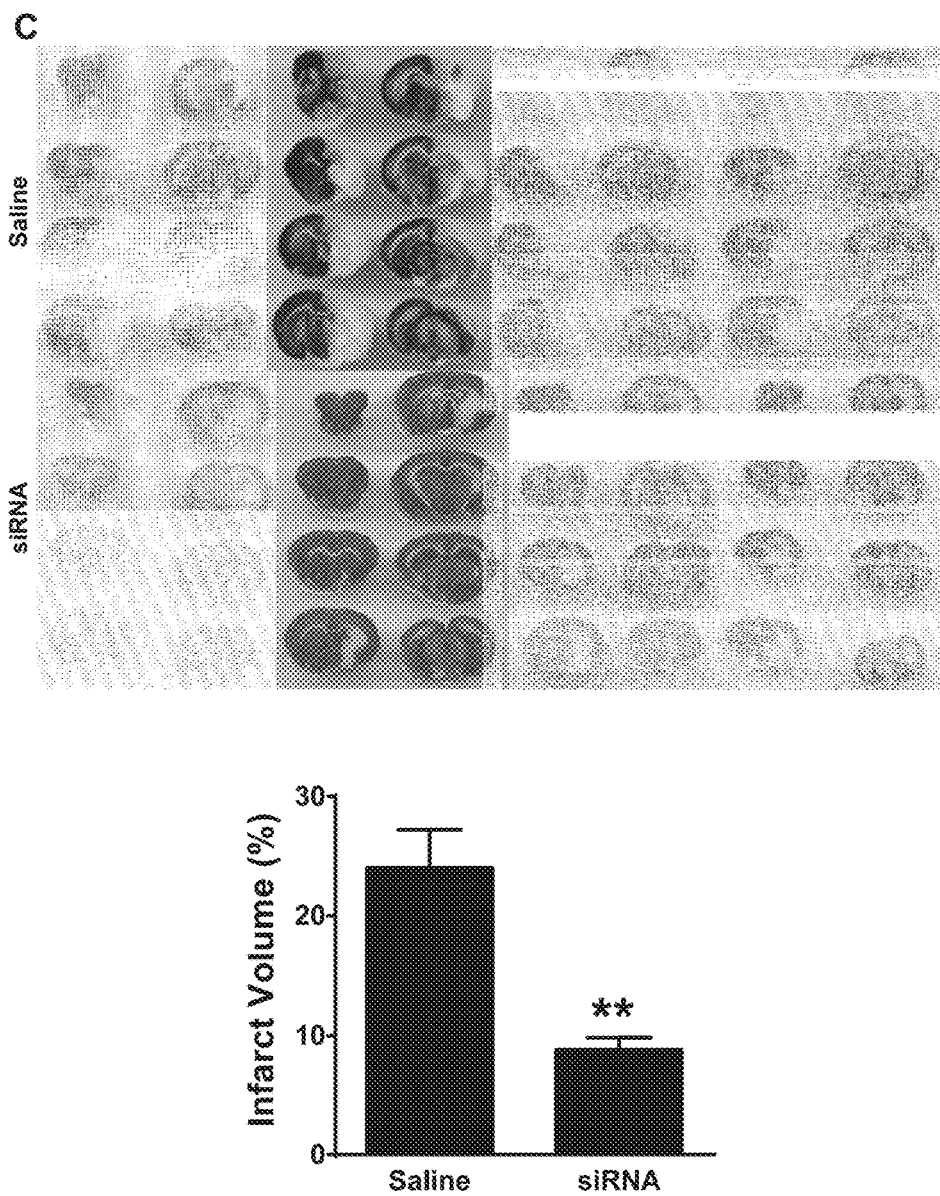

SEQUENCE LISTING

```
<160> NUMBER OF SEQ ID NOS: 15

<210> SEQ ID NO 1
<211> LENGTH: 28
<212> TYPE: PRT
<213> ORGANISM: Rattus norvegicus

<400> SEQUENCE: 1

Gln Asp Arg Ser Ser Asn Cys Ser Ala Glu Arg Gly Ser Trp Ala His
1               5                   10                  15

Pro Glu Gly Pro Val Ala Gly Ser Cys Val Ser Gln
            20                  25

<210> SEQ ID NO 2
<211> LENGTH: 28
<212> TYPE: PRT
<213> ORGANISM: Homo sapiens

<400> SEQUENCE: 2

Arg Asp Ser Asp Ser Asn Cys Ser Ser Glu Pro Gly Phe Trp Ala His
1               5                   10                  15

Pro Pro Gly Ala Gln Ala Gly Thr Cys Val Ser Gln
            20                  25
```

```
<210> SEQ ID NO 3
<211> LENGTH: 28
<212> TYPE: PRT
<213> ORGANISM: Mus musculus

<400> SEQUENCE: 3

Gln Asp Arg Ser Gly Asn Cys Ser Met Glu Arg Gly Ser Trp Ala His
1               5                   10                  15

Pro Glu Gly Pro Val Ala Gly Ser Cys Val Ser Gln
            20                  25

<210> SEQ ID NO 4
<211> LENGTH: 31
<212> TYPE: PRT
<213> ORGANISM: Rattus norvegicus

<400> SEQUENCE: 4

Ala Thr Cys Leu Gln Leu Ala Met Gln Ala Asp Ala Arg Ala Phe Phe
1               5                   10                  15

Ala Gln Asp Gly Val Gln Ser Leu Leu Thr Gln Lys Trp Trp Gly
            20                  25                  30

<210> SEQ ID NO 5
<211> LENGTH: 20
<212> TYPE: DNA
<213> ORGANISM: Rattus norvegicus

<400> SEQUENCE: 5
ctggttctcg ccttcttttg                                           20

<210> SEQ ID NO 6
<211> LENGTH: 20
<212> TYPE: DNA
<213> ORGANISM: Rattus norvegicus

<400> SEQUENCE: 6
catgaagtcg atgcagagga                                           20

<210> SEQ ID NO 7
<211> LENGTH: 21
<212> TYPE: DNA
<213> ORGANISM: Rattus norvegicus

<400> SEQUENCE: 7
cgcuaguagc agcaaaucut t                                         21

<210> SEQ ID NO 8
<211> LENGTH: 21
<212> TYPE: DNA
<213> ORGANISM: Rattus norvegicus

<400> SEQUENCE: 8
agauuugcug cuacuagcgt g                                         21

<210> SEQ ID NO 9
<211> LENGTH: 40
<212> TYPE: DNA
<213> ORGANISM: Rattus norvegicus

<400> SEQUENCE: 9
gcgaattcca ggaccgcagt agtaactgct ctgccgagcg                     40
```

<210> SEQ ID NO 10
<211> LENGTH: 31
<212> TYPE: DNA
<213> ORGANISM: Rattus norvegicus

<400> SEQUENCE: 10
cggtcgactc actgggacac acaggagcct g                                     31

<210> SEQ ID NO 11
<211> LENGTH: 1208
<212> TYPE: PRT
<213> ORGANISM: Rattus norvegicus

<400> SEQUENCE: 11

Met Val Gly Gln Glu Lys Glu Gln Ser Trp Ile Pro Lys Ile Phe Arg
1               5                   10                  15

Lys Lys Val Cys Thr Thr Phe Ile Val Asp Leu His Asp Asp Ala Gly
            20                  25                  30

Gly Thr Leu Cys Gln Cys Gly Gln Pro Arg Asp Ala His Pro Ser Val
        35                  40                  45

Ala Val Glu Asp Ala Phe Gly Ala Ala Val Val Thr Glu Trp Asn Ser
    50                  55                  60

Asp Glu His Thr Thr Glu Lys Pro Thr Asp Ala Tyr Gly Asp Leu Asp
65                  70                  75                  80

Phe Thr Tyr Ser Gly Arg Lys Ser Ser Asn Phe Leu Arg Leu Ser Asp
                85                  90                  95

Arg Thr Asp Pro Ala Thr Val Tyr Ser Leu Val Thr Arg Ser Trp Gly
            100                 105                 110

Phe Arg Ala Pro Asn Leu Val Val Ser Val Leu Gly Gly Ser Glu Gly
        115                 120                 125

Pro Val Leu Gln Thr Trp Leu Gln Asp Leu Leu Arg Arg Gly Leu Val
    130                 135                 140

Arg Ala Ala Gln Ser Thr Gly Ala Trp Ile Val Thr Gly Gly Leu His
145                 150                 155                 160

Thr Gly Ile Gly Arg His Val Gly Val Ala Val Arg Asp His Gln Thr
                165                 170                 175

Ala Ser Thr Gly Gly Ser Lys Val Val Ala Met Gly Val Ala Pro Trp
            180                 185                 190

Gly Val Val Arg Asn Arg Asp Met Leu Ile Asn Pro Lys Gly Ser Phe
        195                 200                 205

Pro Ala Arg Tyr Arg Trp Arg Gly Asp Pro Glu Asp Gly Val Glu Phe
    210                 215                 220

Pro Leu Asp Tyr Asn Tyr Ser Ala Phe Phe Leu Val Asp Asp Gly Thr
225                 230                 235                 240

Tyr Gly Arg Met Gly Gly Glu Asn Arg Phe Arg Leu Arg Phe Glu Ser
                245                 250                 255

Tyr Val Ala Gln Gln Lys Thr Gly Val Gly Gly Thr Gly Ile Asp Ile
            260                 265                 270

Pro Val Leu Leu Leu Leu Ile Glu Gly Asp Glu Lys Met Leu Lys Arg
        275                 280                 285

Ile Glu Asp Ala Thr Gln Ala Gln Leu Pro Cys Leu Leu Val Ala Gly
    290                 295                 300

Ser Gly Gly Ala Ala Asp Cys Leu Val Glu Thr Leu Glu Asp Thr Leu
305                 310                 315                 320

Ala Pro Gly Ser Gly Gly Leu Arg Arg Gly Glu Ala Arg Asp Arg Ile
                325                 330                 335

-continued

```
Arg Arg Tyr Phe Pro Lys Gly Asp Pro Glu Val Leu Gln Ala Gln Val
            340                 345                 350
Glu Arg Ile Met Thr Arg Lys Glu Leu Leu Thr Val Tyr Ser Ser Glu
            355                 360                 365
Asp Gly Ser Glu Glu Phe Glu Thr Ile Val Leu Arg Ala Leu Val Lys
370                 375                 380
Ala Cys Gly Ser Ser Glu Ala Ser Ala Tyr Leu Asp Glu Leu Arg Leu
385                 390                 395                 400
Ala Val Ala Trp Asn Arg Val Asp Ile Ala Gln Ser Glu Leu Phe Arg
            405                 410                 415
Gly Asp Ile Gln Trp Arg Ser Phe His Leu Glu Ala Ser Leu Met Asp
            420                 425                 430
Ala Leu Leu Asn Asp Arg Pro Glu Phe Val Arg Leu Leu Ile Ser His
            435                 440                 445
Gly Leu Ser Leu Gly His Phe Leu Thr Pro Val Arg Leu Ala Gln Leu
            450                 455                 460
Tyr Ser Ala Val Ser Pro Asn Ser Leu Ile Arg Asn Leu Leu Asp Gln
465                 470                 475                 480
Ala Ser His Ala Ser Ser Lys Ser Pro Ala Asn Gly Ala Ala
            485                 490                 495
Glu Leu Arg Pro Pro Asn Val Gly Gln Val Leu Arg Thr Leu Leu Gly
            500                 505                 510
Glu Thr Cys Ala Pro Arg Tyr Pro Ala Arg Asn Thr Arg His Ser Leu
            515                 520                 525
Leu Gly Gln Asp His Arg Glu Asn Asp Ser Leu Leu Met Asp Trp Ala
            530                 535                 540
Asn Met Gln Gln Asp Ala Ser Phe Glu Gln Ala Pro Trp Ser Asp Leu
545                 550                 555                 560
Leu Ile Trp Ala Leu Leu Leu Asn Arg Ala Gln Met Ala Ile Tyr Phe
            565                 570                 575
Trp Glu Lys Gly Ser Asn Ser Val Ala Ser Ala Leu Gly Ala Cys Leu
            580                 585                 590
Leu Leu Arg Val Met Ala Arg Leu Glu Trp Glu Ala Glu Ala Ala
            595                 600                 605
Arg Arg Lys Asp Leu Ala Ala Lys Phe Glu Ser Met Ser Val Asp Leu
            610                 615                 620
Phe Gly Glu Cys Tyr His Asn Ser Glu Tyr Arg Ala Ala Arg Leu Leu
625                 630                 635                 640
Leu Arg Arg Cys Pro Leu Trp Gly Glu Ala Thr Cys Leu Gln Leu Ala
            645                 650                 655
Met Gln Ala Asp Ala Arg Ala Phe Phe Ala Gln Asp Gly Val Gln Ser
            660                 665                 670
Leu Leu Thr Gln Lys Trp Trp Gly Glu Met Asp Ser Thr Asn Pro Ile
            675                 680                 685
Trp Ala Leu Leu Leu Thr Phe Phe Cys Pro Pro Leu Ile Tyr Thr Asn
            690                 695                 700
Leu Ile Leu Phe Arg Lys Ser Glu Glu Pro Thr Gln Lys Asp Leu
705                 710                 715                 720
Asp Phe Asp Met Asp Ser Ser Met Asn Gly Ala Gly Pro Leu Gly Pro
            725                 730                 735
Ala Glu Pro Ser Ala Lys Val Ala Leu Glu Arg Arg Arg Arg
            740                 745                 750
```

-continued

Pro Gly His Thr Leu Cys Cys Gly Cys Ser Lys Arg Trp Ser Tyr
755                 760                 765

Phe Trp Gly Ala Pro Val Thr Ala Phe Leu Gly Asn Val Val Ser Tyr
770                 775                 780

Leu Leu Phe Leu Leu Phe Ala His Val Leu Leu Val Asp Phe Gln
785                 790                 795                 800

Pro Thr Lys Pro Gly Val Phe Glu Leu Leu Leu Tyr Phe Trp Ala Phe
                805                 810                 815

Thr Leu Leu Cys Glu Glu Leu Arg Gln Gly Leu Gly Gly Trp Gly
                820                 825                 830

Thr Leu Ala Asn Gly Gly Pro Gly Pro Gly Lys Ala Pro Leu Arg His
                835                 840                 845

Arg Leu His Leu Tyr Leu Leu Asp Thr Trp Asn Gln Cys Asp Leu Leu
850                 855                 860

Ala Leu Thr Cys Phe Leu Leu Gly Val Gly Cys Arg Leu Thr Pro Gly
865                 870                 875                 880

Leu Phe Asp Leu Gly Arg Thr Val Leu Cys Leu Asp Phe Met Ile Phe
                885                 890                 895

Thr Leu Arg Leu Leu His Ile Phe Thr Val Asn Lys Gln Leu Gly Pro
                900                 905                 910

Lys Ile Val Ile Val Ser Lys Met Met Lys Asp Val Phe Phe Leu
915                 920                 925

Phe Phe Leu Cys Val Trp Leu Val Ala Tyr Gly Val Ala Thr Glu Gly
930                 935                 940

Ile Leu Arg Pro Gln Asp Arg Ser Leu Pro Ser Ile Leu Arg Arg Val
945                 950                 955                 960

Phe Tyr Arg Pro Tyr Leu Gln Ile Phe Gly Gln Ile Pro Gln Glu Glu
                965                 970                 975

Met Asp Val Ala Leu Met Asn Pro Ser Asn Cys Ser Ala Glu Arg Gly
                980                 985                 990

Ser Trp Ala His Pro Glu Gly Pro Val Ala Gly Ser Cys Val Ser Gln
                995                 1000                1005

Tyr Ala Asn Trp Leu Val Val Leu Leu Leu Ile Val Phe Leu Leu
1010                1015                1020

Val Ala Asn Ile Leu Leu Leu Asn Leu Leu Ile Ala Met Phe Ser
1025                1030                1035

Tyr Thr Phe Asn Lys Val His Gly Asn Ser Asp Leu Tyr Trp Lys
1040                1045                1050

Ala Gln Arg Tyr Ser Leu Ile Arg Glu Phe His Ser Arg Pro Ala
1055                1060                1065

Leu Ala Pro Pro Leu Ile Ile Ile Ser His Leu Arg Leu Leu Phe
1070                1075                1080

Lys Trp Leu Arg Arg Cys His Arg Thr Asn Leu Pro Ala Ser Pro
1085                1090                1095

Val Phe Glu His Phe Arg Val Cys Leu Ser Lys Glu Ala Glu Arg
1100                1105                1110

Thr Leu Leu Thr Trp Glu Ser Val His Lys Glu Asn Phe Leu Leu
1115                1120                1125

Ala Gln Ala Arg Asp Lys Arg Asp Ser Asp Ser Glu Arg Leu Lys
1130                1135                1140

Arg Thr Ser Gln Lys Val Asp Thr Ala Leu Lys Gln Leu Gly Gln
1145                1150                1155

-continued

```
Ile Arg Glu Tyr Asp Arg Arg Leu Arg Gly Leu Glu Arg Glu Val
    1160                1165                1170

Gln His Cys Ser Arg Val Leu Thr Trp Met Ala Glu Ala Leu Ser
    1175                1180                1185

His Ser Ala Leu Leu Pro Pro Gly Gly Pro Pro Pro Ser Pro
    1190                1195                1200

Thr Gly Ser Lys Asp
    1205

<210> SEQ ID NO 12
<211> LENGTH: 1214
<212> TYPE: PRT
<213> ORGANISM: Homo sapiens

<400> SEQUENCE: 12

Met Val Val Pro Glu Lys Glu Gln Ser Trp Ile Pro Lys Ile Phe Lys
1               5                   10                  15

Lys Lys Thr Cys Thr Thr Phe Ile Val Asp Ser Thr Asp Pro Gly Gly
            20                  25                  30

Thr Leu Cys Gln Cys Gly Arg Pro Arg Thr Ala His Pro Ala Val Ala
        35                  40                  45

Met Glu Asp Ala Phe Gly Ala Ala Val Val Thr Val Trp Asp Ser Asp
    50                  55                  60

Ala His Thr Thr Glu Lys Pro Thr Asp Ala Tyr Gly Glu Leu Asp Phe
65                  70                  75                  80

Thr Gly Ala Gly Arg Lys His Ser Asn Phe Leu Arg Leu Ser Asp Arg
                85                  90                  95

Thr Asp Pro Ala Ala Val Tyr Ser Leu Val Thr Arg Thr Trp Gly Phe
            100                 105                 110

Arg Ala Pro Asn Leu Val Val Ser Val Leu Gly Gly Ser Gly Gly Pro
        115                 120                 125

Val Leu Gln Thr Trp Leu Gln Asp Leu Leu Arg Arg Gly Leu Val Arg
    130                 135                 140

Ala Ala Gln Ser Thr Gly Ala Trp Ile Val Thr Gly Gly Leu His Thr
145                 150                 155                 160

Gly Ile Gly Arg His Val Gly Val Ala Val Arg Asp His Gln Met Ala
                165                 170                 175

Ser Thr Gly Gly Thr Lys Val Val Ala Met Gly Val Ala Pro Trp Gly
            180                 185                 190

Val Val Arg Asn Arg Asp Thr Leu Ile Asn Pro Lys Gly Ser Phe Pro
        195                 200                 205

Ala Arg Tyr Arg Trp Arg Gly Asp Pro Glu Asp Gly Val Gln Phe Pro
    210                 215                 220

Leu Asp Tyr Asn Tyr Ser Ala Phe Phe Leu Val Asp Asp Gly Thr His
225                 230                 235                 240

Gly Cys Leu Gly Gly Glu Asn Arg Phe Arg Leu Arg Leu Glu Ser Tyr
                245                 250                 255

Ile Ser Gln Gln Lys Thr Gly Val Gly Gly Thr Gly Ile Asp Ile Pro
            260                 265                 270

Val Leu Leu Leu Leu Ile Asp Gly Asp Glu Lys Met Leu Thr Arg Ile
        275                 280                 285

Glu Asn Ala Thr Gln Ala Gln Leu Pro Cys Leu Leu Val Ala Gly Ser
    290                 295                 300

Gly Gly Ala Ala Asp Cys Leu Ala Glu Thr Leu Glu Asp Thr Leu Ala
305                 310                 315                 320
```

```
Pro Gly Ser Gly Gly Ala Arg Gln Gly Glu Ala Arg Asp Arg Ile Arg
            325                 330                 335

Arg Phe Phe Pro Lys Gly Asp Leu Glu Val Leu Gln Ala Gln Val Glu
            340                 345                 350

Arg Ile Met Thr Arg Lys Glu Leu Leu Thr Val Tyr Ser Ser Glu Asp
            355                 360                 365

Gly Ser Glu Glu Phe Glu Thr Ile Val Leu Lys Ala Leu Val Lys Ala
            370                 375                 380

Cys Gly Ser Ser Glu Ala Ser Ala Tyr Leu Asp Glu Leu Arg Leu Ala
385                 390                 395                 400

Val Ala Trp Asn Arg Val Asp Ile Ala Gln Ser Glu Leu Phe Arg Gly
            405                 410                 415

Asp Ile Gln Trp Arg Ser Phe His Leu Glu Ala Ser Leu Met Asp Ala
            420                 425                 430

Leu Leu Asn Asp Arg Pro Glu Phe Val Arg Leu Leu Ile Ser His Gly
            435                 440                 445

Leu Ser Leu Gly His Phe Leu Thr Pro Met Arg Leu Ala Gln Leu Tyr
            450                 455                 460

Ser Ala Ala Pro Ser Asn Ser Leu Ile Arg Asn Leu Leu Asp Gln Ala
465                 470                 475                 480

Ser His Ser Ala Gly Thr Lys Ala Pro Ala Leu Lys Gly Gly Ala Ala
            485                 490                 495

Glu Leu Arg Pro Pro Asp Val Gly His Val Leu Arg Met Leu Leu Gly
            500                 505                 510

Lys Met Cys Ala Pro Arg Tyr Pro Ser Gly Gly Ala Trp Asp Pro His
            515                 520                 525

Pro Gly Gln Gly Phe Gly Glu Ser Met Tyr Leu Leu Ser Asp Lys Ala
            530                 535                 540

Thr Ser Pro Leu Ser Leu Asp Ala Gly Leu Gly Gln Ala Pro Trp Ser
545                 550                 555                 560

Asp Leu Leu Leu Trp Ala Leu Leu Asn Arg Ala Gln Met Ala Met
            565                 570                 575

Tyr Phe Trp Glu Met Gly Ser Asn Ala Val Ser Ser Ala Leu Gly Ala
            580                 585                 590

Cys Leu Leu Leu Arg Val Met Ala Arg Leu Glu Pro Asp Ala Glu Glu
            595                 600                 605

Ala Ala Arg Arg Lys Asp Leu Ala Phe Lys Phe Glu Gly Met Gly Val
            610                 615                 620

Asp Leu Phe Gly Glu Cys Tyr Arg Ser Ser Glu Val Arg Ala Ala Arg
625                 630                 635                 640

Leu Leu Leu Arg Arg Cys Pro Leu Trp Gly Asp Ala Thr Cys Leu Gln
            645                 650                 655

Leu Ala Met Gln Ala Asp Ala Arg Ala Phe Phe Ala Gln Asp Gly Val
            660                 665                 670

Gln Ser Leu Leu Thr Gln Lys Trp Trp Gly Asp Met Ala Ser Thr Thr
            675                 680                 685

Pro Ile Trp Ala Leu Val Leu Ala Phe Cys Pro Pro Leu Ile Tyr
            690                 695                 700

Thr Arg Leu Ile Thr Phe Arg Lys Ser Glu Glu Pro Thr Arg Glu
705                 710                 715                 720

Glu Leu Glu Phe Asp Met Asp Ser Val Ile Asn Gly Glu Gly Pro Val
            725                 730                 735
```

-continued

```
Gly Thr Ala Asp Pro Ala Glu Lys Thr Pro Leu Val Pro Arg Gln
            740                 745                 750

Ser Gly Arg Pro Gly Cys Cys Gly Arg Cys Gly Arg Cys
        755                 760                 765

Leu Arg Arg Trp Phe His Phe Trp Gly Ala Pro Val Thr Ile Phe Met
770                 775                 780

Gly Asn Val Val Ser Tyr Leu Leu Phe Leu Leu Leu Phe Ser Arg Val
785                 790                 795                 800

Leu Leu Val Asp Phe Gln Pro Ala Pro Gly Ser Leu Glu Leu Leu
                805                 810                 815

Leu Tyr Phe Trp Ala Phe Thr Leu Leu Cys Glu Glu Leu Arg Gln Gly
            820                 825                 830

Leu Ser Gly Gly Gly Gly Ser Leu Ala Ser Gly Gly Pro Gly Pro Gly
            835                 840                 845

His Ala Ser Leu Ser Gln Arg Leu Arg Leu Tyr Leu Ala Asp Ser Trp
            850                 855                 860

Asn Gln Cys Asp Leu Val Ala Leu Thr Cys Phe Leu Leu Gly Val Gly
865                 870                 875                 880

Cys Arg Leu Thr Pro Gly Leu Tyr His Leu Gly Arg Thr Val Leu Cys
                885                 890                 895

Ile Asp Phe Met Val Phe Thr Val Arg Leu Leu His Ile Phe Thr Val
                900                 905                 910

Asn Lys Gln Leu Gly Pro Lys Ile Val Ile Val Ser Lys Met Met Lys
            915                 920                 925

Asp Val Phe Phe Phe Leu Phe Phe Leu Gly Val Trp Leu Val Ala Tyr
930                 935                 940

Gly Val Ala Thr Glu Gly Leu Leu Arg Pro Arg Asp Ser Asp Phe Pro
945                 950                 955                 960

Ser Ile Leu Arg Arg Val Phe Tyr Arg Pro Tyr Leu Gln Ile Phe Gly
                965                 970                 975

Gln Ile Pro Gln Glu Asp Met Asp Val Ala Leu Met Glu His Ser Asn
            980                 985                 990

Cys Ser Ser Glu Pro Gly Phe Trp Ala His Pro Pro Gly Ala Gln Ala
            995                 1000                1005

Gly Thr Cys Val Ser Gln Tyr Ala Asn Trp Leu Val Val Leu Leu
        1010                1015                1020

Leu Val Ile Phe Leu Leu Val Ala Asn Ile Leu Leu Val Asn Leu
        1025                1030                1035

Leu Ile Ala Met Phe Ser Tyr Thr Phe Gly Lys Val Gln Gly Asn
        1040                1045                1050

Ser Asp Leu Tyr Trp Lys Ala Gln Arg Tyr Arg Leu Ile Arg Glu
        1055                1060                1065

Phe His Ser Arg Pro Ala Leu Ala Pro Pro Phe Ile Val Ile Ser
        1070                1075                1080

His Leu Arg Leu Leu Leu Arg Gln Leu Cys Arg Arg Pro Arg Ser
        1085                1090                1095

Pro Gln Pro Ser Ser Pro Ala Leu Glu His Phe Arg Val Tyr Leu
        1100                1105                1110

Ser Lys Glu Ala Glu Arg Lys Leu Leu Thr Trp Glu Ser Val His
        1115                1120                1125

Lys Glu Asn Phe Leu Leu Ala Arg Ala Arg Asp Lys Arg Glu Ser
        1130                1135                1140
```

```
Asp Ser Glu Arg Leu Lys Arg Thr Ser Gln Lys Val Asp Leu Ala
1145                1150                1155

Leu Lys Gln Leu Gly His Ile Arg Glu Tyr Glu Gln Arg Leu Lys
    1160                1165                1170

Val Leu Glu Arg Glu Val Gln Gln Cys Ser Arg Val Leu Gly Trp
    1175                1180                1185

Val Ala Glu Ala Leu Ser Arg Ser Ala Leu Leu Pro Pro Gly Gly
    1190                1195                1200

Pro Pro Pro Pro Asp Leu Pro Gly Ser Lys Asp
    1205                1210
```

<210> SEQ ID NO 13
<211> LENGTH: 1213
<212> TYPE: PRT
<213> ORGANISM: Mus musculus

<400> SEQUENCE: 13

```
Met Val Gly Pro Glu Lys Glu Gln Ser Trp Ile Pro Lys Ile Phe Arg
1               5                   10                  15

Lys Lys Val Cys Thr Thr Phe Ile Val Asp Leu Ser Asp Asp Ala Gly
                20                  25                  30

Gly Thr Leu Cys Gln Cys Gly Gln Pro Arg Asp Ala His Pro Ser Val
            35                  40                  45

Ala Val Glu Asp Ala Phe Gly Ala Ala Val Thr Glu Trp Asn Ser
        50                  55                  60

Asp Glu His Thr Thr Glu Lys Pro Thr Asp Ala Tyr Gly Asp Leu Asp
65                  70                  75                  80

Phe Thr Tyr Ser Gly Arg Lys His Ser Asn Phe Leu Arg Leu Ser Asp
                85                  90                  95

Arg Thr Asp Pro Ala Thr Val Tyr Ser Leu Val Thr Arg Ser Trp Gly
                100                 105                 110

Phe Arg Ala Pro Asn Leu Val Val Ser Val Leu Gly Ser Gly Gly
            115                 120                 125

Pro Val Leu Gln Thr Trp Leu Gln Asp Leu Leu Arg Arg Gly Leu Val
    130                 135                 140

Arg Ala Ala Gln Ser Thr Gly Ala Trp Ile Val Thr Gly Gly Leu His
145                 150                 155                 160

Thr Gly Ile Gly Arg His Val Gly Val Ala Val Arg Asp His Gln Thr
                165                 170                 175

Ala Ser Thr Gly Ser Ser Lys Val Val Ala Met Gly Val Ala Pro Trp
            180                 185                 190

Gly Val Val Arg Asn Arg Asp Met Leu Ile Asn Pro Lys Gly Ser Phe
        195                 200                 205

Pro Ala Arg Tyr Arg Trp Arg Gly Asp Pro Glu Asp Gly Val Glu Phe
    210                 215                 220

Pro Leu Asp Tyr Asn Tyr Ser Ala Phe Phe Leu Val Asp Asp Gly Thr
225                 230                 235                 240

Tyr Gly Arg Leu Gly Gly Glu Asn Arg Phe Arg Leu Arg Phe Glu Ser
                245                 250                 255

Tyr Val Ala Gln Gln Lys Thr Gly Val Gly Gly Thr Gly Ile Asp Ile
            260                 265                 270

Pro Val Leu Leu Leu Leu Ile Asp Gly Asp Glu Lys Met Leu Lys Arg
        275                 280                 285

Ile Glu Asp Ala Thr Gln Ala Gln Leu Pro Cys Leu Leu Val Ala Gly
    290                 295                 300
```

```
Ser Gly Gly Ala Ala Asp Cys Leu Val Glu Thr Leu Glu Asp Thr Leu
305                 310                 315                 320

Ala Pro Gly Ser Gly Gly Leu Arg Arg Gly Glu Ala Arg Asp Arg Ile
            325                 330                 335

Arg Arg Tyr Phe Pro Lys Gly Asp Pro Glu Val Leu Gln Ala Gln Val
                340                 345                 350

Glu Arg Ile Met Thr Arg Lys Glu Leu Leu Thr Val Tyr Ser Ser Glu
            355                 360                 365

Asp Gly Ser Glu Glu Phe Glu Thr Ile Val Leu Arg Ala Leu Val Lys
        370                 375                 380

Ala Cys Gly Ser Ser Glu Ala Ser Ala Tyr Leu Asp Glu Leu Arg Leu
385                 390                 395                 400

Ala Val Ala Trp Asn Arg Val Asp Ile Ala Gln Ser Glu Leu Phe Arg
                405                 410                 415

Gly Asp Ile Gln Trp Arg Ser Phe His Leu Glu Ala Ser Leu Met Asp
                420                 425                 430

Ala Leu Leu Asn Asp Arg Pro Glu Phe Val Arg Leu Leu Ile Ser His
            435                 440                 445

Gly Leu Ser Leu Gly His Phe Leu Thr Pro Val Arg Leu Ala Gln Leu
450                 455                 460

Tyr Ser Ala Val Ser Pro Asn Ser Leu Ile Arg Asn Leu Leu Asp Gln
465                 470                 475                 480

Ala Ser His Ala Ser Ser Lys Ser Pro Pro Val Asn Gly Thr Val
            485                 490                 495

Glu Leu Arg Pro Pro Asn Val Gly Gln Val Leu Arg Thr Leu Leu Gly
            500                 505                 510

Glu Thr Cys Ala Pro Arg Tyr Pro Ala Arg Asn Thr Arg Asp Ser Tyr
            515                 520                 525

Leu Gly Gln Asp His Arg Glu Asn Asp Ser Leu Leu Met Asp Trp Ala
530                 535                 540

Asn Lys Gln Pro Ser Thr Asp Ala Ser Phe Glu Gln Ala Pro Trp Ser
545                 550                 555                 560

Asp Leu Leu Ile Trp Ala Leu Leu Leu Asn Arg Ala Gln Met Ala Ile
                565                 570                 575

Tyr Phe Trp Glu Lys Gly Ser Asn Ser Val Ala Ser Ala Leu Gly Ala
            580                 585                 590

Cys Leu Leu Leu Arg Val Met Ala Arg Leu Glu Ser Glu Ala Glu Glu
                595                 600                 605

Ala Ala Arg Arg Lys Asp Leu Ala Ala Thr Phe Glu Ser Met Ser Val
610                 615                 620

Asp Leu Phe Gly Glu Cys Tyr His Asn Ser Glu Glu Arg Ala Ala Arg
625                 630                 635                 640

Leu Leu Leu Arg Arg Cys Pro Leu Trp Gly Glu Ala Thr Cys Leu Gln
                645                 650                 655

Leu Ala Met Gln Ala Asp Ala Arg Ala Phe Phe Ala Gln Asp Gly Val
            660                 665                 670

Gln Ser Leu Leu Thr Gln Lys Trp Trp Gly Met Asp Ser Thr Thr
            675                 680                 685

Pro Ile Trp Ala Leu Leu Leu Ala Phe Phe Cys Pro Pro Leu Ile Tyr
        690                 695                 700

Thr Asn Leu Ile Val Phe Arg Lys Ser Glu Glu Glu Pro Thr Gln Lys
705                 710                 715                 720
```

-continued

Asp Leu Asp Phe Asp Met Asp Ser Ser Ile Asn Gly Ala Gly Pro Pro
            725                 730                 735

Gly Thr Val Glu Pro Ser Ala Lys Val Ala Leu Glu Arg Gln Arg
    740                 745                 750

Arg Arg Pro Gly Arg Ala Leu Cys Cys Gly Lys Phe Ser Lys Arg Trp
        755                 760                 765

Ser Asp Phe Trp Gly Ala Pro Val Thr Ala Phe Leu Gly Asn Val Val
770                 775                 780

Ser Tyr Leu Leu Phe Leu Leu Phe Ala His Val Leu Leu Val Asp
785                 790                 795                 800

Phe Gln Pro Thr Lys Pro Ser Val Ser Glu Leu Leu Leu Tyr Phe Trp
            805                 810                 815

Ala Phe Thr Leu Leu Cys Glu Glu Leu Arg Gln Gly Leu Gly Gly Gly
            820                 825                 830

Trp Gly Ser Leu Ala Ser Gly Gly Arg Gly Pro Asp Arg Ala Pro Leu
        835                 840                 845

Arg His Arg Leu His Leu Tyr Leu Ser Asp Thr Trp Asn Gln Cys Asp
    850                 855                 860

Leu Leu Ala Leu Thr Cys Phe Leu Leu Gly Val Gly Cys Arg Leu Thr
865                 870                 875                 880

Pro Gly Leu Phe Asp Leu Gly Arg Thr Val Leu Cys Leu Asp Phe Met
            885                 890                 895

Ile Phe Thr Leu Arg Leu Leu His Ile Phe Thr Val Asn Lys Gln Leu
        900                 905                 910

Gly Pro Lys Ile Val Ile Val Ser Lys Met Met Lys Asp Val Phe Phe
    915                 920                 925

Phe Leu Phe Phe Leu Cys Val Trp Leu Val Ala Tyr Gly Val Ala Thr
930                 935                 940

Glu Gly Ile Leu Arg Pro Gln Asp Arg Ser Leu Pro Ser Ile Leu Arg
945                 950                 955                 960

Arg Val Phe Tyr Arg Pro Tyr Leu Gln Ile Phe Gly Gln Ile Pro Gln
            965                 970                 975

Glu Glu Met Asp Val Ala Leu Met Ile Pro Gly Asn Cys Ser Met Glu
            980                 985                 990

Arg Gly Ser Trp Ala His Pro Glu Gly Pro Val Ala Gly Ser Cys Val
        995                 1000                1005

Ser Gln Tyr Ala Asn Trp Leu Val Val Leu Leu Leu Ile Val Phe
    1010                1015                1020

Leu Leu Val Ala Asn Ile Leu Leu Leu Asn Leu Leu Ile Ala Met
    1025                1030                1035

Phe Ser Tyr Thr Phe Ser Lys Val His Gly Asn Ser Asp Leu Tyr
    1040                1045                1050

Trp Lys Ala Gln Arg Tyr Ser Leu Ile Arg Glu Phe His Ser Arg
    1055                1060                1065

Pro Ala Leu Ala Pro Pro Leu Ile Ile Ile Ser His Val Arg Leu
    1070                1075                1080

Leu Ile Lys Trp Leu Arg Arg Cys Arg Arg Cys Arg Arg Ala Asn
    1085                1090                1095

Leu Pro Ala Ser Pro Val Phe Glu His Phe Arg Val Cys Leu Ser
    1100                1105                1110

Lys Glu Ala Glu Arg Lys Leu Leu Thr Trp Glu Ser Val His Lys
    1115                1120                1125

```
Glu Asn Phe Leu Leu Ala Gln Ala Arg Asp Lys Arg Asp Ser Asp
    1130                1135                1140
Ser Glu Arg Leu Lys Arg Thr Ser Gln Lys Val Asp Thr Ala Leu
    1145                1150                1155
Lys Gln Leu Gly Gln Ile Arg Glu Tyr Asp Arg Arg Leu Arg Gly
    1160                1165                1170
Leu Glu Arg Glu Val Gln His Cys Ser Arg Val Leu Thr Trp Met
    1175                1180                1185
Ala Glu Ala Leu Ser His Ser Ala Leu Leu Pro Pro Gly Ala Pro
    1190                1195                1200
Pro Pro Pro Ser Pro Thr Gly Ser Lys Asp
    1205                1210

<210> SEQ ID NO 14
<211> LENGTH: 23
<212> TYPE: DNA
<213> ORGANISM: Artificial
<220> FEATURE:
<223> OTHER INFORMATION: GAPDH forward primer

<400> SEQUENCE: 14
gaaggtgaag gtcggagtca acg                                        23

<210> SEQ ID NO 15
<211> LENGTH: 23
<212> TYPE: DNA
<213> ORGANISM: Artificial
<220> FEATURE:
<223> OTHER INFORMATION: GAPDH reverse primer

<400> SEQUENCE: 15
tgccatgggt ggaatcatat tgg                                        23
```

TRPM4 CHANNEL INHIBITORS FOR STROKE TREATMENT

RELATED APPLICATIONS

This application is a national stage filing under 35 U.S.C. 371 of International Application No. PCT/SG2014/000314, filed Jun. 30, 2014, which claims the benefit of Singapore Application No. 201305129-7, filed Jun. 28, 2013. The entire teaching of the above applications are incorporated herein by reference. International Application PCT/SG2014/000314 was published under PCT Article 21(2) in English.

FIELD OF THE INVENTION

The present invention relates to methods for the treatment of ischemic stroke including extension of the therapeutic time window for reperfusion. More particularly, the present invention relates to blocking the function of the TRPM4 channel to improve capillary integrity during the acute and chronic phase of stroke.

BACKGROUND OF THE INVENTION

Stroke is a major health problem worldwide. It is the 4th leading cause of death in Singapore. For those stroke patients who survive, most are likely to be left disabled dud in need of significant rehabilitation. Stroke generates a greater disability impact than any other medical condition and has a huge impact on both the family and society.

There are two types of stroke: ischemic and hemorrhagic. Ischemic stroke, which accounts for more than 80% of all stroke incidences, is attributed by the atherosclerotic occlusion or embolism within an artery, commonly the middle cerebral artery. Focal ischemic stroke with sufficient severity and duration leads to infarction and persistent neurological dysfunction.

Reperfusion is the only potent therapy for acute ischemic stroke. Reperfusion aims to lyse the thrombus with recombinant tissue-type plasminogen activator (rt-PA) or other mechanical devices. Reperfusion therapy is best given within a very narrow time window (<4.5 hours after stroke onset). After that, reperfusion greatly increases cerebral edema and the risk of hemorrhagic transformation which are mainly caused by vascular damage. As very few stroke patients can arrive at hospitals and be diagnosed within this time frame, less than 5% of patients receive reperfusion therapy. Therefore, the focus of acute stroke treatment is to extend the therapeutic time window. However, numerous attempts from both pharmaceutical companies and stroke research community have failed to achieve this goal.

Transient receptor potential melastatin 4 (TRPM4) (see, for example, SEQ ID NOs: 11-13) is a voltage-dependent, non-selective monovalent cation channel. It is impermeable to $Ca^{2+}$, activated by elevated cytosolic $Ca^{2+}$, and modulated by ATP [Vennekens R, Nilius B., *Handb Exp Pharmacol*, 269-85 (2007b)]. TRPM4 belongs to the mammalian TRP superfamily. TRPM4 and TRPM5 are unique because they only conduct monovalent cations, whereas most other TRP channels are permeable to both monovalent and divalent ions. TRPM4 is important for the function of immune cells, including dendritic, mast, and T cells [e.g., Vennekens R, et al., *Nat Immunol* 8, 312-20 (2007a)]. When activated, TRPM4 can depolarize the membrane potential and regulate $Ca^{2+}$ homeostasis by decreasing the driving force for $Ca^{2+}$ entry. Gain-of-function mutations in TRPM4 are associated with familial heart disease [Kruse M, et al., *J Clin Invest*, 119, 2737-44 (2009)]. TRPM4 also participates in the pathophysiology of spinal cord injury (SCI) and experimental autoimmune encephalomyelitis (EAE) [Gerzanich V, et al., *Nat Med*, 15, 185-91 (2009); Schattling B, et al., *Nat Med*, 18, 1805-11 (2012)]. Ectopic expression of TRPM4 has been found in capillaries after SCI and in neurons after EAE. Activation of TRPM4 in SCI and EAE results in unchecked ion influx and subsequently leads to oncotic cell death.

Cerebral edema following brain injury is bound to cell death. Edema resulting from ischemic stroke leads to tissue damage and worsens neurological functions. Recently, upregulation of the non-selective cation channel $NC_{Ca-ATP}$ was observed in neurovascular cells, including astrocytes, neurons, and vascular endothelia, after ischemic stroke [Simard J M, et al., *Nat Med*, 12, 433-40 (2006)]. Enhanced $NC_{Ca-ATP}$ current can lead to unchecked $Na^+$ entry, subsequently oncotic cell death, and is believed to cause brain edema [Kahle K T, et al., *Physiology (Bethesda)*, 24, 257-65 (2009)]. The current exhibits many properties similar to those of TRPM4; including a smaller single-channel conductance, permeability to $Na^+$ and $Cs^+$, and activation by intracellular $Ca^{2+}$ [Simard J M, et al., *Nat Med*, 12, 433-40 (2006)].

The $NC_{Ca-ATP}$ current is also involved in other central nervous system injuries, including traumatic brain injury, spinal cord injury, and subarachnoid hemorrhage [Simard J M, et al., *J Neurosurg*, 113, 622-9 (2010)]. However, studies of $NC_{Ca-ATP}$ channel in stroke have mainly focused on the sulfonylurea receptor-1 (SUR1), an auxiliary subunit of $K_{ATP}$ channels [Simard J M, et al., *Nat Med*, 12, 433-40 (2006)]. After CNS injury, SUR1 has been found upregulated in neurons, astrocytes, and endothelial cells, and the expression is not coupled with $K_{ATP}$ functions. There is evidence that SUR1 can associate with TRPM4, and it is believed that blocking SUR1 with a sulfonylurea such as glibenclimide could inhibit the SUR1/TRPM4 channel and salvage brain tissues after injury [Walcott B P, et al., *Neurotherapeutics* 9:65-72 (2012)]. However, TRPM4 homomers are not sensitive to glibenclamide and there are contradicting reports on whether SUR1 binds TRPM4 directly and whether glibenclimide has a therapeutic effect on stroke [Sala-Rabanal M, et al., *J Biol Chem* 287:8746-56 (2012); Woo S K, et al., *J Biol Chem* M112.428219 (2012); Favilla C G, et al., *Stroke* 42:710-5 (2011); Kunte H, et al., *Ann Neurol* 72:799-806 (2012)].

After the acute stage, the focus of stroke therapy is to promote angiogenesis and neurogenesis, aiming to improve functional recovery and quality of life of patients. As neurological deficits are severe and always lead to disability among stroke survivors, there is also an urgent need to improve current chronic treatment for stroke recovery.

In view of the above deficiencies; it is desirable to provide a method for extending the window for acute therapy by reducing cerebral edema, and improve current therapy for stroke recovery.

The role of TRPM4 after ischemic stroke is unclear. Rat permanent and transient middle cerebral artery occlusion models (MCAO) were used to investigate the expression and functions of TRPM4 in ischemic stroke and the possibility of inhibiting TRPM4 was tested.

SUMMARY OF THE INVENTION

The TRPM4 inhibitors identified in this study appear to have sufficient clinical efficacy for development into agents for stroke treatment.

Accordingly, in a first aspect, the present invention provides an isolated antibody or fragment thereof specific to transient receptor potential melastatin 4 (TRPM4) protein (represented by, for example, SEQ ID NOs 11-13), wherein the antibody specifically binds to a peptide sequence which lies between S5 and the P-loop of the TRPM4 protein and inhibits TRPM4 activity.

In a preferred embodiment of the invention, the antibody or fragment thereof is raised using a TRPM4 peptide selected from the group comprising a peptide consisting of the amino acid sequence SEQ ID NO: 1, a peptide consisting of the amino acid sequence SEQ ID NO: 2 and a peptide consisting of the amino acid sequence SEQ ID NO: 3, or an antigenic variant or fragment thereof.

Another preferred embodiment of the invention relates to the antibody or fragment thereof being a polyclonal, monoclonal or humanized antibody.

Another preferred embodiment of the invention relates to the antibody or fragment thereof being a mouse-human chimeric antibody.

A preferred embodiment of the invention relates to a mouse-human chimeric antibody, wherein the mouse VH domain is ligated to human IgG1 CH domain and the mouse VL domain is ligated to human light chain kappa constant (CL) domain.

In another preferred embodiment of the invention, the antibody or fragment thereof inhibits TRPM4 currents.

In another preferred embodiment of the invention, the antibody or a fragment thereof is for use in treating ischemic stroke.

According to another aspect of the invention, there is provided a method of treating ischemic stroke, comprising administering to a subject in need thereof an efficacious amount of at least one TRPM4 inhibitor.

In a preferred embodiment of the method of the invention, the at least one inhibitor is an antibody or a fragment thereof which specifically binds to TRPM4, or is a TRPM4-specific siRNA.

In another preferred embodiment of the method of the invention, the antibody is a polyclonal antibody, a monoclonal antibody, or a humanized antibody or a fragment thereof.

In another preferred embodiment of the method of the invention, the siRNA comprises, essentially consists of, or consists of a sense oligonucleotide. SEQ ID NO: 7 and an antisense oligonucleotide SEQ ID NO: 8.

In another preferred embodiment of the method of the invention, the at least one TRPM4 inhibitor is administered in combination with one or more thrombolytic agents.

In another preferred embodiment of the method of the invention, the at least one TRPM4 inhibitor is administered during the acute stage and/or the chronic stage.

In another preferred embodiment of the method of the invention, the treatment increases angiogenesis in the subject.

In another preferred embodiment of the method of the invention, the treatment reduces infarct volume in the subject.

In another preferred embodiment of the method of the invention, the treatment extends the therapeutic time window for reperfusion.

In another aspect of the invention, there is provided the use of at least one TRPM4 inhibitor for the preparation of a medicament for the treatment of ischemic stroke.

In a preferred embodiment of the use of the invention, the at least one inhibitor is an antibody or a fragment thereof which specifically binds to the sequence which lies between S5 and the P-loop of TRPM4, or is a siRNA which specifically inhibits TRPM4 activity.

In another preferred embodiment of the use of the invention, the antibody is a polyclonal antibody, a monoclonal antibody, or a humanized antibody, or a fragment thereof.

In another preferred embodiment of the use of the invention, the siRNA comprises, essentially consists of, or consists of a sense oligonucleotide SEQ ID NO: 7 and an antisense oligonucleotide SEQ ID NO: 8.

In another aspect of the invention, there is provided a process for the production of an antibody or fragment thereof, comprising administering to a mammal a TRPM4 peptide, variant or antigenic fragment thereof as defined herein.

In a preferred embodiment, the peptide is selected from the group comprising a peptide consisting of the amino acid sequence SEQ ID NO: 1, a peptide consisting of the amino acid sequence SEQ ID NO: 2 and a peptide consisting of the amino acid sequence SEQ ID NO: 3, or an antigenic variant or fragment thereof.

Another aspect of the invention provides an isolated nucleic acid molecule capable of expressing the TRPM4 antigenic peptide, variant or fragment thereof according to any aspect of the present invention.

In yet another aspect of the present invention there is provided at least one plasmid or vector comprising the nucleic acid molecule according to any aspect of the present invention. Another aspect of the invention provides a kit for treating stroke, the kit comprising at least one antibody or a fragment thereof as defined herein and/or at least one siRNA as defined herein and, optionally, at least one thrombolytic agent.

BRIEF DESCRIPTION OF THE FIGURES

FIG. 1: Amino acid sequence (SEQ ID NO: 11) of rat TRPM4 channel protein. Peptide sequences used to generate antibodies are highlighted and underlined.

FIG. 2: Amino acid sequence (SEQ ID NO: 12) of human Isoform 1 TRPM4b channel protein. Peptide sequences corresponding to those used to generate antibodies are highlighted and underlined.

FIG. 3: Amino acid sequence of mouse Isoform 1 TRPM4 channel protein (SEQ ID NO: 13). Peptide sequences corresponding to those used to generate antibodies are highlighted and underlined.

FIG. 5: Up-regulation of TRPM4 in the vascular endothelium within the penumbra region 1 day after MCAO. (A) DAB staining of the capillaries with vWF in the contralateral and ipsilateral regions. Scale bar: 200 μm. Capillary counting showed significant angiogenesis in the ipsilateral region. ***P<0.0001, n=25. (B) Representative staining of TRPM4 and co-localization with vWF in the contralateral and ipsilateral regions. Scale bar: 50 μm.

FIG. 6: (A), Immunohistochemical staining of vWF (red) and TRPM4 (green) in the sham-operated rat brain. (B), Co-staining of vWF (red) and TRPM5 (green) within penumbra region 1 day after MCAO.

FIG. 9: (A), HUVEC cell number count after treatment with different dines of 9-phenamthrol. (B), HUVEC cell number count after treatment with 5 μM 9-phenamthrol. A significant cell loss was observed after 24 hours exposure to hypoxic condition. There is no difference between control cells and 9-phenanthrol treated cells under both normoxia and hypoxia. (C), MTT assay showed no difference between cells and 9-phenanthrol treated cells, similar to cell counting study.

DETAILED DESCRIPTION OF THE INVENTION

Definitions

Figure 4:
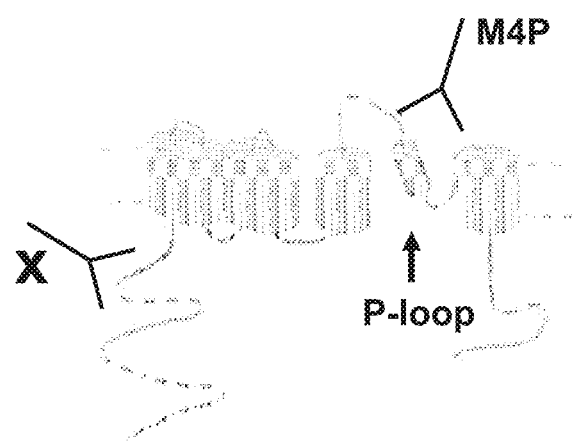
FIG. 4: Schematic showing the region of the TRPM4 protein where the peptide epitope is derived from, and where antibody M4P binds to inhibit activity.

Certain terms employed in the specification, examples and appended claims are collected here for convenience.

The terms "amino acid" or "amino acid sequence," as used herein, refer to an oligopeptide, peptide, polypeptide, or protein sequence, or a fragment of any of these, and to naturally occurring or synthetic molecules. The term "TRPM4 peptide sequence", as used herein, refers to an antigenic peptide epitope used to generate TRPM4 inhibitory antibodies.

In this context, "fragments" refers to a TRPM4 peptide epitope according to the invention which has been reduced in length by one or more amino acids and which retains antigenic activity of TRPM4 sufficient to raise antibodies that inhibit TRPM4 activity.

The term 'variants' of the oligopeptide, peptide, polypeptide, or protein sequence as used herein, refers to changes that may be made to the native amino acid sequence that still allow the production of antibodies that inhibit TRPM4 activity. For example, one or more conservative amino acid substitutions may be made to the TRPM4 peptide epitope used according to the invention. Basis for this can be found in that the antibody M4P binds to the rat, mouse and human TRPM4 channels which vary in amino acids 1, 3-5, 9, 11, 13, 18, 20, 21 and 24 of the epitope peptide (Table 1). Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

An antibody is any immunoglobulin, including antibodies and fragments thereof that bind to a specific epitope. The antibody according to the invention may be prepared against the sequence which lies between S5 and the P-loop of the TRPM4 protein. More specifically, the target TRPM4 polypeptide epitope comprises, essentially consists of, or consists of the amino acid sequence SEQ ID NO: 1, SEQ ID NO: 2 or SEQ ID NO: 3 (Table 1) or a variant or fragment thereof. Such antibodies include, but are not limited to polyclonal, monoclonal, chimeric, humanised, single chain, Fab, Fab', F(ab)' fragments and/or F(v) portions of the whole antibody which are capable of binding to TRPM4 and inhibiting its activity. The polypeptide or oligopeptide used to immunize an animal (e.g., a mouse, a rat, or a rabbit) can be derived from the translation of RNA, an expression construct such as a plasmid, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "humanized antibody," as used herein, refers to antibody molecules in which the amino acid sequence in the non-antigen binding regions has been altered so that the antibody more closely resembles a human antibody, and still retains its original binding ability.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term 'variant', as used in the context of the present invention is intended to describe variations to the amino acid sequence of the TRPM4 polypeptide epitope that do not remove the antigenicity of the polypeptide in terms of eliciting antibodies which bind to and inhibit TRPM4 activity. Variants include conservative amino acid substitutions.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, one or more amino acid residues in a TRPM4 polypeptide epitope comprising, essentially consisting of, or consisting of the amino acid sequence QDRSSNCSAERGSWAHPEGPVAGSCVSQ (SEQ ID NO: 1), RDSDSNCSSEPGFWAHPPGAQAGTCVSQ (SEQ ID NO: 2) or QDRSGNCSMERGSWAHPEGPVAGSCVSQ (SEQ ID NO: 3) or a fragment thereof may be replaced with one or more other amino acid residues from the same side chain family without significantly reducing the antigenicity of the epitope or deviating significantly from the scope of the present invention.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay. As used herein, the term "oligonucleotide" is substantially equivalent to the terms "amplimers," "primers," "oligomers," and "probes," as these terms are commonly defined in the art.

The term "antisense," as used herein, refers to any composition containing a nucleic acid sequence which is complementary to a specific polynucleotide sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can' refer to the antisense strand, and the designation "positive" can refer to the sense strand.

The term "small interfering RNA" (siRNA), as used herein, refers to small pieces of double-stranded (ds) RNA, usually about 21 nucleotides long, with 3' overhangs (2 nucleotides) at each end that can be used to interfere with the translation of proteins by binding to and promoting the degradation of messenger RNA (mRNA) at specific sequences. In doing so, they prevent the production of specific proteins based on the nucleotide sequences of their corresponding mRNA. Suitable siRNA's for use according to the invention include SEQ ID NOs: 7-8 (Table 1).

The term "treatment", as used in the context of the invention refers to prophylactic, ameliorating, therapeutic or curative treatment.

The term "comprising" as used in the context of the invention refers to where the various components, ingredients, or steps, can be conjointly employed in practicing the present invention. Accordingly, the term "comprising" encompasses the more restrictive terms "consisting essentially of" and "consisting of." With the term "consisting essentially of" it is understood that the epitope/antigen of the present invention "substantially" comprises the indicated sequence as "essential" element. Additional sequences may be included at the 5' end and/or at the 3' end. Accordingly, a polypeptide. "consisting essentially of" sequence X will be novel in view of a known polypeptide accidentally comprising the sequence X. With the term "consisting of" it is understood that the polypeptide, polynucleotide and/or antigen according to the invention corresponds to at least one of the indicated sequence (for example a specific sequence indicated with a SEQ ID Number or a homologous sequence or fragment thereof).

A person skilled in the art will appreciate that the present invention may be practiced without undue experimentation according to the method given herein. The methods, techniques and chemicals are as described in the references given, or from protocols in standard biotechnology and molecular biology text books.

In a first aspect, the present invention provides an isolated antibody or fragment thereof specific to transient receptor potential melastatin 4 (TRPM4) protein, wherein the antibody specifically binds to a peptide sequence which lies between S5 and the P-loop of the TRPM4 protein and inhibits TRPM4 activity. Suitable peptide sequences (SEQ ID NOs: 1-3) are shown in Table 1.

TABLE 1

Polypeptide and polynucleotide sequences of the invention.

| Protein/nucleotide | Sequences | SEQ ID NO |
|---|---|---|
| Rat TRPM4 epitope | QDRSSNCSAERGSWAHPEGPVAGSCVSQ | 1 |
| Human TRPM4 epitope | RDSDSNCSSEPGFWAHPPGAQAGTCVSQ | 2 |
| Mouse TRPM4 epitope | QDRSGNCSMERGSWAHPEGPVAGSCVSQ | 3 |
| Rat, mouse, human TRPM4 | ATCLQLAMQADARAFFAQDGVQSLLTQKWWG | 4 |
| Forward primer detection | 5'-CTGGTTCTCGCCTTCTTTTG-3' | 5 |
| Reverse primer detection | 5'-CATGAAGTCGATGCAGAGGA-3' | 6 |
| siRNA sense | 5'-CGCUAGUAGCAGCAAAUCUtt-3' | 7 |
| siRNA antisense | 5'-AGAUUUGCUGCUACUAGCGtg-3' | 8 |
| Forward primer cloning | GCGAATTCCAGGACCCCACTAGTAACTGCTCTGCCGAGCG | 9 |
| Reverse primer cloning | CGGTCGACTCACTGGGACACACAGGAGCCTG | 10 |

A preferred embodiment of the invention relates to the antibody or fragment thereof being a polyclonal, monoclonal or humanized antibody.

Antibodies raised to this region of the TRPM4 protein according to the invention have been found to inhibit TRPM4 activity. The antibodies of the invention bind to and inhibit TRPM4 homomer channels, but may also be capable of inhibiting any channel formed by TRPM4.

More specifically, the antibody or fragment thereof is preferably raised using a TRPM4 peptide sequence selected from the group comprising or consisting of the rat peptide sequence SEQ ID NO: 1, the human peptide sequence SEQ ID NO: 2 and the mouse peptide sequence SEQ ID NO: 3, or an antigenic variant or fragment thereof. The term 'variant' has been defined above.

Preferably the peptide sequence used to raise the TRPM4 inhibitory antibody consists of the sequence SEQ ID NO: 1, SEQ ID NO: 2 or SEQ ID NO: 3; more preferably the peptide consists of SEQ ID NO: 1 or SEQ ID NO: 2. Antibodies raised to the rat peptide of SEQ ID NO: 1 bind to TRPM4 channels from rat, human and mouse species.

TRPM4 channel peptides from other species which are homologous to the peptide sequences of SEQ ID NOs: 1-3 may also be suitable as antigens for use according to the invention. Thus the scope of the invention is intended to encompass such homologous peptides.

It is important in the clinical setting that the antibody does not itself elicit an immune response in the subject. Therefore, it has become common practice to minimise or eliminate the immunogenicity of antibodies raised in other species used for human treatment by humanizing them.

Techniques have been developed for the production of humanized antibodies [See, e.g., Queen, U.S. Pat. No. 5,585,089 and Winter, U.S. Pat. No. 5,225,539, which are incorporated herein by reference in their entirety]. An immunoglobulin light or heavy chain variable region consists of a "framework" region interrupted by three hyper variable regions, referred to as complementarity determining regions (CDRs). The extent of the framework region and CDRs have been precisely defined [see, "Sequences of Proteins of Immunological Interest", Kabat, E. et al., U.S. Department of Health and Human Services (1983), incorporated herein by reference in their entirety]. Briefly, humanized antibodies are antibody molecules from non-human species having one or more CDRs from the non-human species and a framework region from a human immunoglobulin molecule.

One type of antibody or fragment thereof suitable for human use is a mouse-human chimeric antibody.

Techniques developed for the production of "chimeric antibodies" [Morrison, it al., Proc Natl Acad Sci, 81: 6851-6855 (1984); Neuberger, et al., Nature 312: 604-608 (1984); Takeda, et al., Nature, 314: 452-454 (1985), incorporated herein by reference in their entirety] by splicing the genes from a mouse antibody molecule of appropriate antigen specificity together with genes from a human antibody molecule of appropriate biological activity can be used. For example, the genes from a mouse antibody molecule specific for a TRPM4 epitope can be spliced together with genes from a human antibody molecule of appropriate biological activity. A chimeric antibody is a molecule in which different portions are derived from different animal species, such as those having a variable region derived from a murine mAb and a human immunoglobulin constant region [See, e.g., Cabilly et al., U.S. Pat. No. 4,816,567; and Boss et al., U.S. Pat. No. 4,816,397, which are incorporated herein by reference in their entirety].

Preferably, the mouse VH domain is ligated to human IgG1 CH domain and the mouse VL domain is ligated to human light chain kappa constant (CL) domain.

In one aspect of the invention, there is provided an antibody or a fragment thereof wherein said antibody or fragment inhibits TRPM4 currents. TRPM4 forms homomer channels and, as described herein, there is some evidence albeit conflicting that TRPM4 may also associate with SUR1 to form a channel. The data shown herein indicates the antibody of the invention binds to TRPM4 homomer channels.

In a preferred embodiment of the invention, there is provided an antibody or a fragment thereof for use in treating ischemic stroke. The antibody or fragment thereof binds to TRPM4 to inhibit TRPM4 activity. More specifically, the antibody or fragment thereof binds to a TRPM4 epitope selected from the group comprising, essentially consisting of, or consisting of the amino acid sequence SEQ ID NO: 1, SEQ ID NO: 2 and SEQ ID NO: 3 or a variant or fragment thereof.

In a preferred embodiment of the invention, there is provided a method of treating ischemic stroke, comprising administering to a subject in need thereof an efficacious amount of at least one TRPM4 inhibitor. Preferably the at least one inhibitor is an antibody or a fragment thereof which specifically binds to TRPM4, or is a TRPM4-specific siRNA.

The at least one TRPM4 inhibitor may be administered in combination with one or more thrombolytic agents. Thrombolytic agents are only used for ischemic stroke. The most commonly used drug for thrombolytic therapy is tissue plasminogen activator (tPA), but other drugs such as Lanoteplase, Reteplase, Staphylokinase, Streptokinase (SK), Tenecteplase and Urokinase can do the same thing. tPA is an enzyme found naturally in the body that converts, or activates, plasminogen to dissolve a blood clot. It is normally administered intra venously (IV) to the stroke patient during the acute phase and should be given within 3 to 4.5 hours of symptom onset.

In a preferred embodiment, the at least one TRPM4 inhibitor is administered during the acute stage and/or the chronic stage. More preferably, administration is during the acute stage.

From previous few studies on therapeutic antibodies for stroke, the dose of antibody for IV injection in the rat stroke model is about. 200 µg. The IV dose of an antibody used in a failed human trail was 160 mg for a loading dose and subsequently 40 mg for maintenance for 4 days.

Preferably, the antibody is a polyclonal antibody, a mouse monoclonal antibody, or a humanized monoclonal antibody as described above, or a fragment thereof.

Various procedures known in the art may be used for the production of polyclonal antibodies to the polypeptide of the invention, or immunogenic fragment thereof. For the production of antibody, various host animals can be immunised by injecting the polypeptide or an immunogenic variant or fragment thereof, including but not limited to rabbits, mice, rats, sheep, goats, etc. In one embodiment, the peptide of the invention or variant, or fragment thereof can be conjugated to an immunogenic carrier, e.g., bovine serum albumin (BSA) or keyhole limpet hemocyanin (KLH). The peptide of the invention or immunogenic variant or fragment may be further combined with any adjuvant known in the art [for example, Hood et al., in Immunology, p. 384, Second Ed., Benjamin/Cummings, Menlo Park, Calif., 1984, herein incorporated by reference].

In particular, the polyclonal antibody may be produced by a method comprising the steps:
immunising an animal with a polypeptide consisting of the sequence SEQ ID NO: 1, or an immunogenic variant or fragment thereof;
isolating antibodies from said animal; and
screening the isolated antibodies with the polypeptide; thereby identifying a polyclonal antibody that specifically binds to a polypeptide comprising the sequence SEQ ID NO: 1.

An example of the method used for the production of an antibody of the present invention is given in Example 1, which provides a method used for the production of polyclonal antibody M4P using New Zealand white rabbits.

For the preparation of monoclonal antibodies directed towards the polypeptide of the invention or, immunogenic variant or fragment thereof, any technique that provides for the production of antibody molecules by continuous cell lines in culture may be used. These include, but are not limited to, the hybridoma technique originally developed by Kohler et al., Nature, 256: 495-497 (1975), as well as the trioma technique, the human B-cell hybridoma technique [Kozbor et al., Immunology Today, 4:72, (1983)], and the EBV-hybridoma technique to produce human monoclonal antibodies [Cole et al., in Monoclonal Antibodies and Cancer Therapy, pp. 77-96, Alan R. Liss, Inc., 1985]. Immortal, antibody-producing cell lines can be created by techniques other than fusion, such as direct transformation of B lymphocytes with oncogenic DNA, or transfection with Epstein-Barr virus, [e.g., Hammerling et al., "Monoclonal Antibodies And T-cell Hybridomas" (1981); also U.S. Pat. No. 4,341,761; U.S. Pat. No. 4,399,121; U.S. Pat. No. 4,427,783; U.S. Pat. No. 4,444,887; U.S. Pat. No. 4,451,570; U.S. Pat. No. 4,466,917; U.S. Pat. No. 4,472,500; U.S. Pat. No. 4,491,632; or U.S. Pat. No. 4,493,890]:

In particular, the monoclonal antibody can be produced according to the method comprising the steps:
immunising an animal with a polypeptide consisting of the sequence SEQ ID NO: 1, or an immunogenic variant or fragment thereof;
isolating antibody-producing spleen cells and fusing them with immortalised (myeloma) cells in the presence of PEG to form hybridoma cells;
culturing the hybridoma cells and isolating clonal anti-TRPM4 monoclonal antibody producing cell lines; and
isolating from the clonal cell lines a monoclonal antibody that specifically binds to the polypeptide sequence SEQ ID NO: 1 on TRPM4.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting the binding of a secondary antibody or reagent to the primary antibody. In a further embodiment, the secondary antibody is labelled. Many means are known in the art for detecting the binding in an immunoassay and are within the scope of the present invention. For example, to select antibodies which recognize a specific epitope of a polypeptide of the invention (for example, any one of SEQ ID NOS: 1 to 3), one may assay generated hybridomas for a product which binds to a polypeptide fragment containing such an epitope. For selection of an antibody specific to a polypeptide according to the invention from a particular species of animal, one can select on the basis of positive binding with the polypeptide of the invention expressed by or isolated from cells of that species of animal.

In a preferred embodiment of the invention there is provided a method of treating ischemic stroke with a siRNA, wherein the siRNA comprises or consists of a sense oligonucleotide SEQ ID NO: 7 and an antisense oligonucleotide SEQ ID NO: 8.

In a preferred embodiment of the invention, treatment with a TRPM4 inhibitor increases angiogenesis in the subject.

In another preferred embodiment of the invention, treatment with a TRPM4 inhibitor reduces infarct volume in the subject.

In a preferred embodiment of the invention, treatment with a TRPM4 inhibitor extends the therapeutic time window for reperfusion.

In another aspect of the invention there is provided the use of at least one TRPM4 inhibitor for the preparation of a medicament for the treatment of ischemic stroke. In a preferred embodiment, the at least one inhibitor is an antibody or a fragment thereof which specifically binds to the sequence which lies between S5 and the P-loop of TRPM4, or is a siRNA which specifically inhibits TRPM4 activity.

Preferably the antibody is a polyclonal antibody, a monoclonal antibody, or a humanized antibody or an antigen-binding fragment thereof. The monoclonal antibody may be a mouse monoclonal antibody, and the humanized antibody may be a humanized monoclonal antibody.

In a preferred embodiment, the siRNA comprises a sense oligonucleotide comprising or consisting of the sequence SEQ ID NO: 7 and an antisense oligonucleotide comprising or consisting of the sequence SEQ ID NO: 8 (Table 1). The siRNA may be synthesized by known methods or purchased, for example, from Ambion, Life Technologies Corporation, USA.

In yet another aspect of the present invention there is provided a pharmaceutical composition comprising a TRPM4 inhibitory antibody or fragment thereof according to any aspect of the present invention and, optionally a thrombolytic agent as hereinbefore described.

The pharmaceutical composition may further comprise a pharmaceutically acceptable carrier, excipient, adjuvant, diluent and/or detergent. Such formulations therefore include, in addition to the antibody, a physiologically acceptable carrier or diluent, possibly in admixture with one or more other agents such as other antibodies, thrombolytic agents or drugs, such as an antibiotic. Suitable carriers include, but are not limited to, physiological saline, phosphate buffered saline, phosphate buffered saline glucose and buffered saline. Alternatively, the antibody or fragment thereof may be lyophilized (freeze dried) and reconstituted for use when needed by the addition of an aqueous buffered solution as described above. Routes of administration are routinely intravenous.

Another aspect of the invention provides a process for the production of an antibody or fragment thereof according to any aspect of the invention, comprising administering to a mammal a TRPM4 peptide or antigenic variant or fragment thereof as hereinbefore described.

In a preferred embodiment, the peptide is selected from the group comprising or consisting of a peptide consisting of the amino acid sequence SEQ ID NO: 1, a peptide consisting of the amino acid sequence SEQ ID NO: 2 and a peptide consisting of the amino acid sequence SEQ ID NO: 3, or an antigenic variant or fragment thereof. Preferably the peptide consists of the sequence SEQ ID NO: 1 or SEQ ID NO: 2.

The peptides of the invention may be produced for immunization purposes synthetically or via expression constructs which encode them. An example of a suitable expression vector is the bacterial plasmid pGEX-4T-1 (Amersham Pharmacia Biotech, now GE Healthcare Life Sciences), which encodes a fusion protein with a thrombin cleavage site.

Suitable oligonucleotide primers for use in amplifying and cloning TRPM4 peptide into pGEX-4T-1 include: forward primer SEQ ID NO: 9 and reverse primer SEQ ID NO: 10 (Table 1).

Modifications and changes may be made in the structure of the DNA segments which encode the peptides and still obtain a functional molecule that encodes a peptide that can elicit an immune response. The nucleic acid molecules according to the invention can contain naturally occurring sequences, or sequences that differ from those that occur naturally, but, due to the degeneracy of the genetic code, encode the same peptide (for example, the peptides with SEQ ID NOs: 1-3). The nucleic acid molecules according to the invention may have sequence changes that cause a conservative amino acid substitution that does not significantly reduce the TRPM4 inhibitory activity of antibodies directed to such altered peptides. The isolated nucleic acid molecules according to the invention encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location).

The DNA may be expressed in a suitable host to produce a polypeptide comprising the TRPM4 peptide according to any aspect of the invention. Thus, the DNA encoding the peptide of the invention may be used in accordance with known techniques, to construct an expression vector, which is then used to transform an appropriate host cell for the expression and production of the peptide according to the invention.

In yet another aspect of the present invention there is provided at least one plasmid or vector comprising the nucleic acid molecule according to any aspect of the present invention.

In yet another aspect of the present invention there is provided a kit for treating stroke, the kit comprising at least one antibody or a fragment thereof according to any aspect of the invention and/or at least one siRNA according to any aspect of the invention and, optionally, at least one thrombolytic agent.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russell, Molecular Cloning: A Laboratory Manual, Cold Springs Harbor Laboratory, New York (2001).

Materials and Methods

Animal Model

This study was approved and performed in accordance with the guidelines of the Institutional Animal Care and Use Committee of the National Neuroscience Institute, Singapore. As per the approved protocol, male Wistar rats weighing approximately 300 g were subjected to permanent or transient middle cerebral artery occlusion (MCAO). Prior to surgery, the animals were anesthetized with ketamine (75 mg/kg) and xylazine (10 mg/kg) intra-peritoneally. Under an operating microscope, the left common carotid artery was exposed and temporarily ligated using a vascular clip (Aesculap, B. Braun, Germany). Next, the left external carotid artery (ECA) and internal carotid artery (ICA) were dissected from the surrounding tissues. Occipital artery and superior thyroid artery (branches of ECA) were occluded. The ECA was then ligated with a 4-0 silk suture. The ICA was also free from the adjacent vagus nerve. Subsequently, a loose knot was made at the ECA stump near the bifurcation with a 4-0 silk suture. The extra cranial branch of ICA was temporarily ligated with a vascular clip as well. The distal end of the ECA was cut and a silicon coated filament (0.37 mm, Cat #403756PK10, Doccol Corp, Redlands, Calif.) was introduced into the ICA through the ECA stump. Subsequently, the suture around the ECA stump was tightened around the intraluminal filament, and the micro vascular clip was removed. The filament was then gently advanced from the ECA to the ICA lumen for approximately 18-20 mm. The ligation on the CCA was released after the suture on the ECA-intraluminal filament was tightened. The sham-operated rats underwent similar procedures, except for the insertion of the suture. For the transient MCAO model, the filament was removed at 2 hours or 5 hours after occlusion.

Infarct Volume Measurement 2,3,5-Triphenyltetrazolium chloride (TTC) staining relies on the ability of the dehydrogenase enzymes and cofactors present in the living tissue to react with tetrazolium salts, the main component of the TTC solution, to form a formazan pigment. After the animals were euthanized, the brains were collected, and the cerebellum and overlying membranes were removed. The brain was sectioned into 2-mm-thick coronal slices using a brain-sectioning block. The sections were stained with 0.1% TTC (Sigma, USA) solution at 37° C. for 30 minutes and then preserved in 4% formalin solution. The sections were scanned and the infarct size was analyzed using an image analyzer system (Scion image from Windows, Microsoft).

Immunofluorescent Staining

The animals were euthanized and perfused with saline followed by 4% paraformaldehyde (PFA). The brains were then collected and post-fixed with 4% PFA for 2 hours. Dehydration was subsequently carried out by immersing the brain in a 15% sucrose solution, followed by 30% sucrose solution. Next, the rat brain was cryosectioned at 20 μm of thickness. After washing with 0.2% Triton X-100 phosphate buffered saline (PBST), 100 μl of the blocking serum (10% goat serum and 1% bovine serum albumin in 0.2% PBST) was added to the sections for 1 hour. The brain sections were then incubated with primary antibodies overnight at 4° C. The primary antibodies used in the study are: anti-TRPM4 (sc-27540, Santa Cruz, Calif., USA), anti-NeuN (MAB377, Millipore), anti-GFAP (IF03L, Calbiochem, Millipore), anti-smooth muscle actin (CBL171, Millipore), and anti-vWF (AB7356, Millipore, Mass., USA). On the following day, the tissue sections were washed 3 times with TNT wash buffer (0.1 M tris-HCl buffer pH7.5 containing 0.15 M NaCl and 0.05% Tween 20). The slides were incubated with secondary antibodies for 1 hour at room temperature. After washing 3 times of wash buffer, the slides were mounted with FluorSave™ reagent (Merck, Germany). The results were visualized by a laser scanning confocal microscope (Fluoview BX61, Olympus). The negative control underwent an identical procedure with the exception of the primary antibody incubation; no positive signal was observed.

Capillary Counting

Capillary counting was conducted stereologically. Every fifth 100-μm brain section across the entire region of infarction was counted. For random sampling, six fields per brain section were randomly chosen under a confocal microscope under 40-× magnification. The number of blood vessels was measured by counting the number of elongated tube-like structures with positive vWF immunoreactivity.

Western Blot

Tissues from the penumbra region and the contralateral control sites were collected from the TTC-stained brain slices as described earlier [Zhao H, et al., *J Neurosci*, 25, 9794-806 (2005)], incorporated herein by reference. The brain tissues were homogenized in 300 μl of HEPES lysis buffer (20 mM HEPES, 137 mM NaCl, 1% Iriton X-100, 1U % glycerol, 1.5 mM MgCl2, 1 mM EGTA) with freshly added protease inhibitors (1:50 dilution, Roche Diagnostics). The homogenized samples were then centrifuged at 14000 rpm for 15 minutes, and the supernatants were collected. Protein concentration was determined using the Bradford assay. For western blot analysis, 200 μg of lysate (with 2× protein loading dye) was separated on an 8% SDS-PAGE gel. The gel was then transferred overnight at 30 V onto a PVDF membrane at 4° C. Subsequently, the membrane was blocked with 1% BSA in 1×PBS+0.1% Tween 20 for 1 hour and probed with an anti-TRPM4 goat polyclonal antibody (1:2000 dilution, SC27540, Santa Cruz Biotechnology) overnight at 4° C. The next day, the membrane was washed 3 times with 0.1% Tween 20 in 1×PBS for 10 minutes. The membrane was then probed with a goat secondary antibody conjugated to HRP (1:5000 dilution, A5420, Sigma Aldrich) for 1 hour. After washing, the TRPM4 band was detected using the Amersham ECL Western Blotting Analysis System (RPN2109, GE Healthcare).

Human Umbilical Vein Endothelial Cells (HUVECs) Culture and Hypoxia Induction

HUVECs (Lonza, Wokingham, UK) were cultured at 37° C. with 5% $CO_2$. The culture medium is endothelial growth medium-2 (EGM-2) consisting of endothelial basal medium (EBM), supplemented with 2% fetal bovine serum, hydrocortisone, hFGF, VEGF, R3-IGF-1, ascorbic acid, HEGF, GA-1000, and heparin (Lonza, Wokingham, UK). Cells at passage 6-10 were used for experiments. HUVECs were subjected to oxygen/glucose deprivation (OGD). To achieve supplement deprivation, EGM-2 was changed to EBM without fetal bovine serum or growth supplements. Hypoxia was induced by culturing the cells in a hypoxic chamber (Stem Cell Technologies, Vancouver, Canada) with 1% $O_2$ and 5% $CO_2$ at 37° C. for 24 hours.

HEK Cell Transfection with Mouse TRPM4 and Prolonged Exposure to M4P HEK293 cells were transiently transfected with mouse TRPM4 using lipofectamine 2000 (lifetechnologies). Positive cells are in green color labeled with GFP. M4P antibody was applied into the culture medium and harvested at different time points (15 min-2 days) for in vitro studies on the binding of M4P to TRPM4 channel on cell membrane. Control rabbit IgG was used as a control.

Immunofluorescent staining was used to study the surface binding of M4P. Primary antibody was omitted, while goat anti-rabbit secondary antibody was applied for staining. For hypoxia treatment, M4P or control IgG was added into the culture medium and the cells were incubated under Oxygen-Glucose deprivation for 12 hr-2 days. The cell survival was measured with Trypan blue and MTT assay.

TRPM4 Channel Currents in Mouse TRPM4 Transfected HEK Cells Exposed to M4P

Cells were transfected as described above. Whole-cell currents were recorded under voltage clamp with Axopatch 200B amplifier (Molecular Devices Corp. Sunnyvale, Calif., USA). Data were digitized at 10 kHz and filtered at 1 kHz. The pClamp 10.2 software was used for data acquisition and analysis. The internal pipette solution contained (in millimole/liter): CsCl 140, NaCl 5, MgCl2 1, BAPTA 1, CaCl2 0.83, and pH 7.2 adjusted with CsOH. The bath solution contained (in millimole/liter): NaCl 140, CsCl 5, CaCl2 2, MgCl2 1, glucose 10, HEPES 10, and pH 7.4 adjusted with NaOH.

Trypan Blue Exclusion and MTT Assay

Cell viability was determined using the trypan blue exclusion method. The cells were trypsinised and incubated with trypan blue. The number of cells was quantified by light microscopy using a haemocytometer chamber and is expressed as the percentage of viable cells. The 3-(4,5-dimethylthiazol-2-yl)-2,5-diphenyltetrazolium bromide (MTT) colorimetric assay (Roche, Switzerland) was performed to assess cell viability. Cell viability was quantified by the amount of MTT reduction. The cells were incubated with anhydrous MTT for 4 hours, and the product was solubilized in a DMSO solution. The optical density was measured at 540 nm. The data is expressed as the percentage of viable cells.

Tube Formation

HUVECs were divided into the following groups: Normoxia; Normoxia+5 µM 9-phenanthrol (Sigma); Hypoxia; and Hypoxia+5 µM 9-phenanthrol. A 24-well culture plate was precoated with 250 µl of growth factor-reduced Matrigel (Sigma, USA) at 37° C. for 30 minutes. 24 hours after OGD, $4\times10^4$ cells (in 300 µl of EGM-2) from each group were seeded onto the Matrigel-coated plates. The formation of capillary structures was examined under a light microscope after 4 hours. This study was replicated more than 4 times.

Reverse Transcriptase PCR

Total RNA was extracted using the TRIzol reagent (Invitrogen, Life Technologies Corporation, USA) according to the manufacturer's protocol. Superscript III (Invitrogen, Life Technologies Corporation, USA) was used to generate first strand cDNA. The PCR was performed as follows: a denaturation step at 95° C. for 5 min; 35 cycles of 94° C. for 30 seconds, 60° C. for 45 seconds, and 72° C. for 30 seconds; and a final extension step at 72° C. for 10 min. GAPDH was used as the endogenous control. The primers used for TRPM4 were as follows: 5'-CTGGTTCTCGCCT-TCTTTTG-3' (forward; SEQ ID NO: 5; Table 1) and 5'-CATGAAGTCGATGCAGAGGA-3' (reverse; SEQ ID NO: 6; Table 1); and GAPDH: 5'-GAAGGTGAAGGTCG-GAGTCAACG-3' (forward; SEQ ID NO: 14) and 5'-TGC-CATGGGTGGAATCATATTGG-3' (reverse; SEQ ID NO: 15).

In Vivo siRNA Delivery

TRPM4 in vivo Ready siRNA was purchased from Ambion, Life Technologies Corporation, USA. The sequences were as follows: sense 5'-CGCUAGUAGCAG-CAAAUCUtt-3' (SEQ ID NO: 7) and antisense 5'-AGAUUUGCUGCUACUAGCGtg-3' (SEQ ID NO: 8). Immediately after operation, the rats received a loading dose of 19 nmole siRNA intravenously. Subsequently, 6 nmole siRNA was given via the jugular vein through an implanted mini-osmotic pump (Alzet, Durect Corporation). The infusion rate was 7.8 µl/hour for 24 hours.

Behavioral Analysis

Motor function after MCAO was evaluated using a rotarod apparatus (Ugo Basile, Italy). The performance of the rats was measured by observing the latency with which the rats fell off the rotarod. Three days before the surgery, the rats received 3 training trials each day with 15-minute intervals. The accelerating rotarod was set from 4 to 80 rpm within 10 minutes. The mean duration of time that the animals remained on the device was recorded 1 day before MCAO as an internal baseline control. At different time points following surgery, the mean duration of latency was recorded and compared to the internal baseline control.

Antibody Production

The procedure for polyclonal antibody production was described before [Liao P, et al., *J Biol Chem* 279: 50329-35 (2004)]. In brief, part of the extracellular domain of rat TRPM4 (FIG. 1; SEQ ID NO: 11), consisting of the amino acid sequence QDRSSNCSAERGSWAHPEGPVAG-SCVSQ (SEQ ID NO: 1; Table 1), corresponding to amino acids 949-952 and 985-1008 of the mature protein (FIG. 1; SEQ ID NO: 11; NCBI Accession# NP_001129701 XP_574447) was cloned in frame into the plasmid expression vector pGEX-4T-1. The primers used for cloning were: Forward primer: GCGAATTCCAGGACCGCAGTAG-TAACTGCTCTGCCGAGCG (SEQ ID NO: 9; Table 1) and Reverse primer: CGGTCGACTCACTGGGACACACAG-GAGCCTG (SEQ ID NO: 10; Table 1). Part of the intracellular domain before the first transmembrane segment of rat TRPM4, corresponding to the amino acid sequence ATCLQLAMQADARAFFAQDGVQSLLTQKWWG (SEQ ID NO: 4) and amino acids 650-680 of the mature protein (FIG. 1; SEQ ID NO: 11) and identical to the sequences in human and mouse TRPM4 (FIGS. 2-3; SEQ ID NOs: 12-13), was also used to generate antibodies. GST-fused protein was extracted from bacteria and purified with glutathione-agarose (Sigma). Purified protein was used to immunize female New Zealand White rabbit once a month. Complete Freund's adjuvant (Sigma) was first injected for immunization, and incomplete Freund's adjuvant was used in subsequent injections once a month. Serum collected from rabbits was pre-absorbed with GST protein to remove non-specific antibodies, and polyclonal antibody was affinity-purified from immobilized TRPM4 protein with an IgG elution buffer (Pierce). The eluted antibody concentration was 1 µg/µl and the 'extracellular domain' antibody was named M4PAb. Serum from rabbits before immunization was used as pre-immune control.

Epitope for Humanized Antibody Production

The epitope from rat TRPM4 targeted by M4P antibody lies between S5 and the P-loop of the TRPM4 channel and corresponds to amino acids 949-952 and 985-1008 of SEQ ID NO: 11 (shown schematically in FIG. 4).

Antibody M4P was found to also bind to, and inhibit, TRPM4 on human cells. The corresponding amino acid sequence of the human TRPM4 channel is RDSDSNC-SSEPGFWAHPPGAQAGTCVSQ (SEQ ID NO: 2) corresponding to amino acids 955-958 and 991-1014 of the mature isoform 1 of TRPM4b (FIG. 2; SEQ ID NO: 12).

Humanized Antibody Production Against TRPM4 Channel

Methods for generating rabbit and mouse monoclonal antibodies are known, as are methods for humanizing them

[Cianfriglia M, et al., *Hybridoma;* 2(4): 451-7 (1983); Riechmann L, et al., *Nature* 332(6162): 323-7 (1988); Verhoeyen M, et al., *Science* 239(4847):1534-6 (1988), incorporated herein by reference].

Stage I: Antibody Sequencing

Based on the study on rat TRPM4 channel with polyclonal antibody M4P, the amino acid sequence of human TRPM4 suitable for generating humanized antibody is RDSDSNC-SSEPGFWAHPPGAQAGTCVSQ (SEQ ID NO: 2). This polypeptide is produced and injected into BALB/c mice as the antigen over 3-4 weeks. The sera is then evaluated for anti-TRPM4 responses by analyzing protein-protein interaction in, for example an ELISA assay. Following that, antibody-producing murine splenocytes are fused with myeloma cells and clonal anti-TRPM4 antibody producing hybridoma cell lines are selected.

The mouse monoclonal antibody against human TRPM4 can be characterized by western blot, in vitro binding assay, electrophysiological study, and therapeutic efficacy on cultured cells as well as in rodent stroke models. Western blot will be carried out using cell lines expressing human TRPM4 and samples from human stroke patients. A binding assay can be carried out by incubating cultured TRPM4 expressing cells with the mouse monoclonal antibody. The surface binding is studied by immunostaining. Additionally, the antibody is injected into MCAO rats to determine whether the antibody binds to the endothelium following stroke. Standard Trypan blue exclusion and MTT assays can then be used to evaluate whether the mouse monoclonal antibody can protect cultured endothelial cells from hypoxic treatment. The therapeutic efficacy is evaluated by measuring the tissue loss following the administration of the therapeutic monoclonal antibody. Further characterization of the antibody involves using patch clamp methods, as described in [Nilius B, et al., *J Biol Chem,* 280(24): 22899-906 (2005)] and herein incorporated by reference, to determine whether the antibody can block TRPM4 currents.

Stage II: Antibody Humanization

Bioinformatics (sequence analysis and modeling) software is used to blend the antibody variable regions from stage I to human donor sequences, creating a panel of humanized heavy and light chains. The humanized chains are then codon optimized for expression in a mammalian system and synthesized (Assay Biotechnology, CA, US). Selections of human constant domain sequences are available and the isotype, class, and subclass of the final antibody can also be specified at this stage.

Stage III: Small Scale Transient Transfection

Each humanized antibody is cloned into a proprietary expression vector for small scale transient transfection using known methods [for example, Karagiannis P, et al., *Cancer Immunol Immunother* 58:915-30 (2009)], incorporated herein by reference. Each construct will undergo small scale expression and purification; the resulting antibodies are tested for affinity to the target as described above.

Stage IV: Stable Cell Line Development

The selected humanized, antibody is then used to generate a stable cell line using a mammalian gene expression system including dihydrofolatereductase or glutamine synthetase amplification systems and the ubiquitous chromatin opening element technologies as described, for example, by Chandrashekran A, et al., [*FEBS Open Bio* 4: 266-75 (2014)], incorporated herein by reference. Once satisfied with the antibody characteristics the cell line can be further optimized for high yield expression and validated for scale-up.

Statistics

All of the results are presented as the mean±S.E.M. Data were graphed using Prism, version 4 (GraphPad Software, CA). Student's t test was used to compare two sample means and one way ANOVA followed by Dunnett's post hoc tests was used to compare the means of data from three or more groups. The results were considered significant if $P<0.05$.

Results

Upreaulation of TRPM4 in the Vascular Endothelium after MCAO

To investigate the role of TRPM4 in ischemic stroke, the middle cerebral artery in rats was permanently occluded. The infarction was located in ipsilateral cortex and striatum (left hemisphere in this study). DAB staining of the capillaries with the endothelial marker von Willebrand factor (vWF) in the contralateral and ipsilateral regions indicated prominent angiogenesis in the penumbra region 1 day post stroke (FIG. 5A). Endothelial vWF staining was stronger in the penumbra region than in the contralateral brain tissues possibly due to endothelial activation and/or dysfunction after stroke [De Meyer S F, et al., *Stroke,* 43, 599-606 (2012)].

Using a TRPM4-specific antibody, strong staining of TRPM4 was detected in the penumbra region that was co-labeled with vWF 1 day post. MCAO (FIG. 5B). TRPM4 was almost undetectable in the vascular endothelium in the uninjured contralateral hemisphere (FIG. 5B) and sham-operated brain (FIG. 6A). Another TRPM channel, TRPM5, which is structurally similar to TRPM4, was not expressed in the endothelium (FIG. 6B).

Western blot analysis revealed a two-fold upregulation of TRPM4 in the penumbra region (FIG. 4a) as compared to the contralateral region. The rat TRPM4 is approximately 135 kDa, suggesting that this protein represents the longer TRPM4b isoform [Nilius B, et al., *J Biol Chem,* 278, 30813-20 (2003)]. The same antibody was able to detect the mouse TRPM4 protein which was expressed in HEK cells as a positive control, confirming the specificity of the antibody for TRPM4. We continuously observed the size of rat TRPM4 was slightly smaller than the mouse TRPM4.

Figure 7:
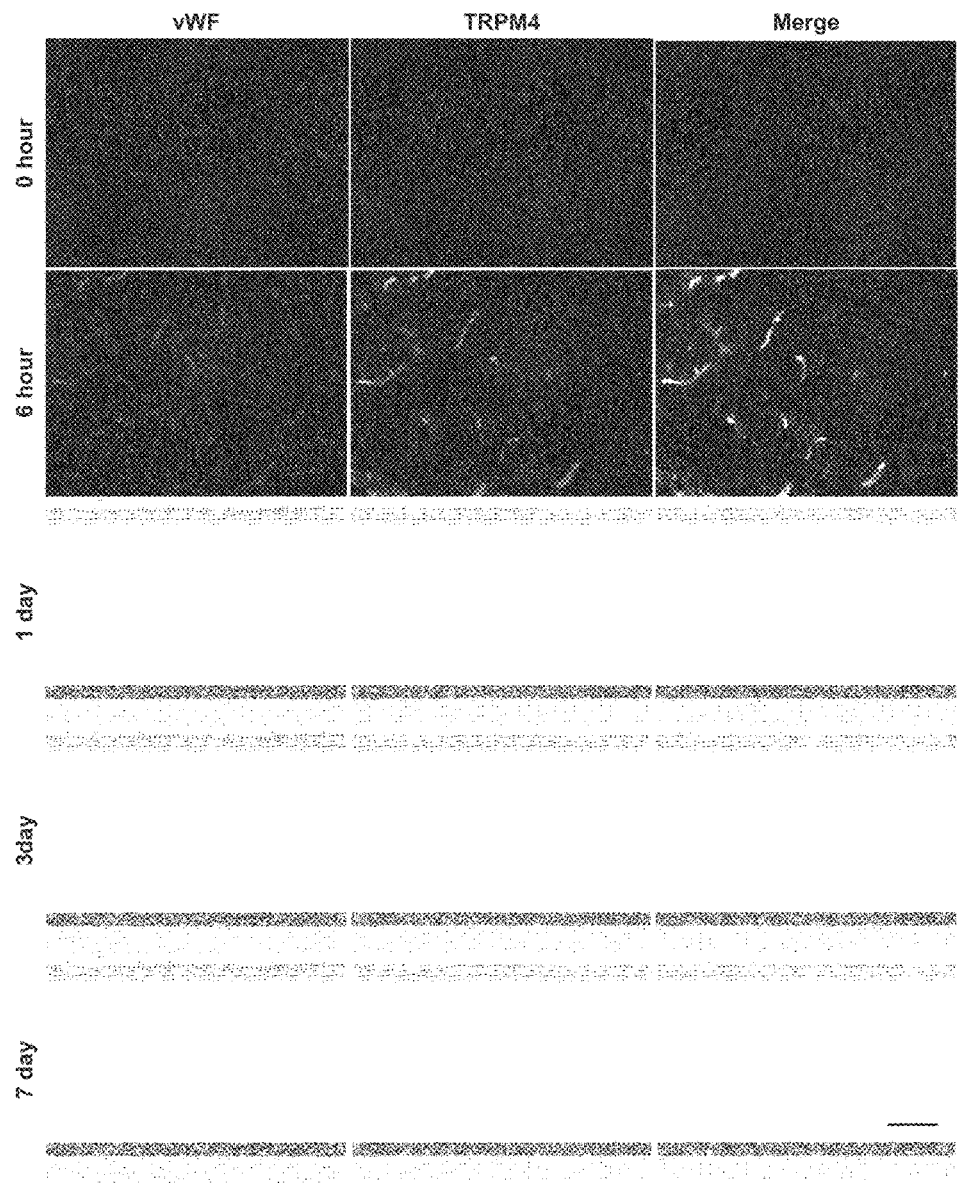
FIG. 7: Time-dependent expression of TRPM4 in the endothelium within the penumbra region after MCAO. Co-staining for TRPM4 and vWF was performed at 0 hour, 6 hours, 1 day, 3 days, and 7 days post operation. Scale bar: 50 μm.

The expression of TRPM4 was further studied in the vascular endothelium within the penumbra at the following time points post MCAO: 0 hour, 6 hour, 1 day, 3 days, and 7 days (FIG. 7). Strong TRPM4 staining was observed in the endothelium as early as 6 hours. The expression levels remained prominent at 1 day post operation. The almost complete colocalization of TRPM4 with vWF indicated that the majority of the endothelial cells within the penumbra region expressed high levels of TRPM4 following stroke. However, by day 3, TRPM4 expression began to decrease gradually. Many vWF-positive cells did not express TRPM4. Furthermore, vascular fragmentation was observed within penumbra region after stroke induction, a typical sign of the loss of vascular integrity. This fragmentation was prominent by day 3 and correlated with the reduced expression of TRPM4. Thus, TRPM4 upregulation in the vascular endothelium may contribute to capillary death post stroke.

Figure 8:
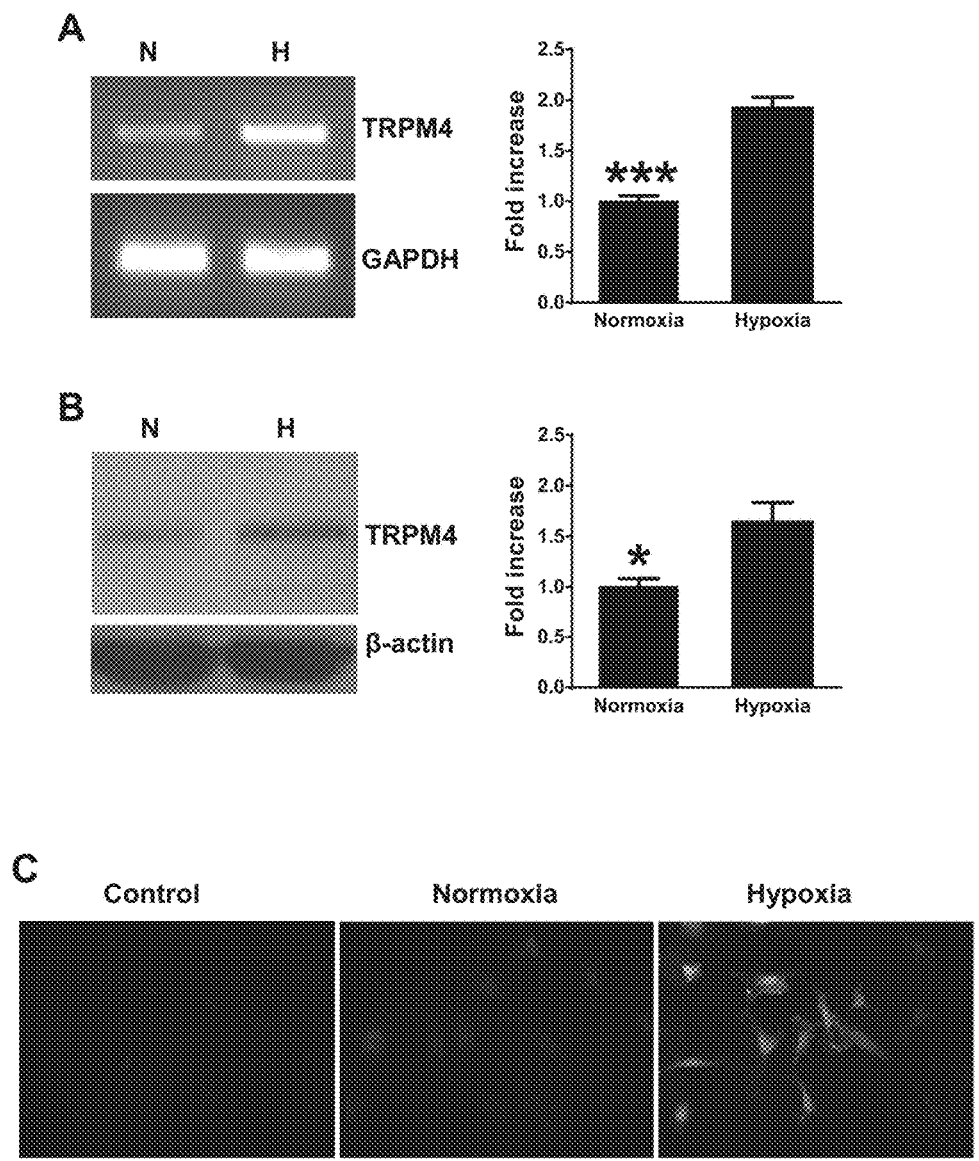
FIG. 8: The expression and function of TRPM4 in human umbilical vein endothelial cells (HUVECs). (A) RT-PCR for TRPM4 in HUVECs 1 day after OGD. GAPDH was used as a loading control. N, normoxia; H, hypoxia. After normalization to GAPDH, TRPM4 was significantly increased in HUVECs after ODG treatment. ***P<0.001, n=4. (B) Western blot for TRPM4 in HUVECs 1 day after OGD. β-actin was used as a loading control. N, normoxia; H, hypoxia. After normalization to β-actin, TRPM4 was significantly increased in HUVECs after ODG treatment. *P<0.05, n=4. (C) Immunofluorescence staining of TRPM4 (green) in HUVECs 1 day after hypoxic induction. The nuclei were labeled with DAPI (blue). Scale bar: 20 μm. (D) The effects of 5 μM of 9-phenanthrol on tube formation in HUVECs after OGD. 9-phenanthrol treatment significantly increased tube branches after OGD (n=4). N-C: normoxia control; N-P: normoxia with 9-phenanthrol; H-C: hypoxia control; H-P: hypoxia with 9-phenanthrol. *P<0.05; ***P<0.001.

In Vitro Blockade of TRPM4 in Human Umbilical Vein Endothelial Cells (HUVECs) Induces Tube Formation This hypothesis was tested in HUVECs under oxygen/glucose deprivation (OGD). The cells were exposed to hypoxic conditions and starved of glucose and serum/growth factors. After 24 hours of OGD, significant cell death occurred. A two-fold increase of TRPM4 mRNA by RT-PCR (FIG. 8A) and a 1.7-fold increase of TRPM4 protein by Western blot (FIG. 8B) were observed after OGD treatment. Such increase was further confirmed by immunofluorescence staining (FIG. 8C).

To test the functional impact of TRPM4 on HUVECs, the cells were incubated with the TRPM4-specific blocker 9-phenanthrol. This blocker does not affect the TRPM5 channel [Grand T, et al., *Br J Pharmacol*, 153, 1697-705 (2008)], another TRPM channel with similar electrophysiological properties to TRPM4 [Vennekens R, Nilius B. *Handb Exp Pharmacol*, 269-85 (2007b); Nilius B, et al., *Physiol Rev*, 87, 165-217 (2007)]. A study was performed in which 9-phenantrol with the concentration ranged from 0.1 µM to 30 µM was added to HUVECs. No difference was observed in cell death between 0.1 µM and 5 µM. Cell death became prominent when 10 µM 9-phenanthrol was added to the culture medium. Very few cells survived treatment with 30 µM 9-phenanthrol (FIG. 9A). Thus, 5 µM 9-phenanthrol was used to treat HUVECs. Unexpectedly, 9-phenanthrol treatment did not reduce cell death after OGD (FIGS. 9B and C). However, a large enhancement of tube formation was observed on Matrigel by 9-phenanthrol treatment after OGD (FIG. 8D). This in vitro study shows that blocking TRPM4 improves endothelial functions under hypoxic conditions.

In Vivo TRPM4 Knockdown Enhances Angiogenesis and Reduces Infarction after MCAO

To demonstrate that TRPM4 is critical for vascular endothelial functions in vivo, a siRNA was used against rat TRPM4 in the animal model of MCAO. A total of 25 nmoles of siRNA was delivered into rats with a body weight of 300 g. A single dose of 19 nmoles was injected intravenously post operation and the remaining 6 nmoles was delivered into the jugular vein with an osmotic pump for 24 hours. Intravenous delivery reduces the loss of siRNA during absorption via other routes and maximizes contact with the endothelium.

Figure 10:
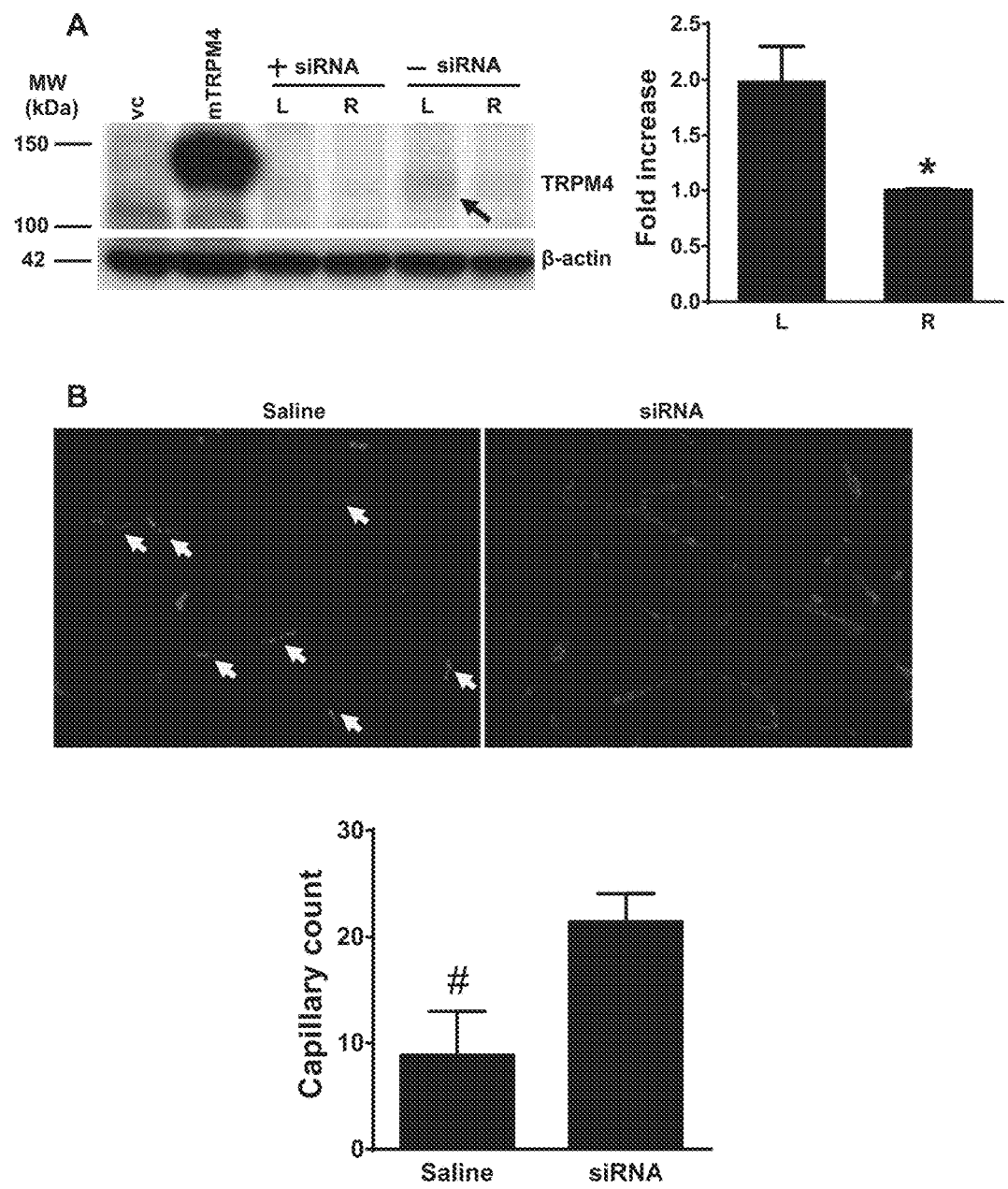
FIG. 10: Knockdown of TRPM4 in vivo enhances angiogenesis and reduces infarct volume after MCAO in rats. (A) Representative Western blot of TRPM4 in rat brains 1 day post MCAO. HEK 293 cells transfected with mouse TRPM4 (mTRPM4) were used as the positive controls and HEK 293 cells transfected with GFP vector alone (vc) were used as the negative control. Samples from ipsilateral penumbra region (L) and corresponding contralateral region (R) with saline (−siRNA) or siRNA treatment (+siRNA) were probed with an antibody against TRPM4. The protein size of the rat TRPM4 (indicated by the arrow) was slightly smaller than the control mouse TRPM4. Without siRNA treatment, a two-fold increase of TRPM4 expression was found in the penumbra region (L). *P<0.05; n=4. In vivo siRNA application successfully inhibited TRPM4 up-regulation within the penumbra region. (B) Staining of the penumbra region with vWF showed the fragmentation of capillaries (indicated by the arrows) in the saline-treated rats 3 days post MCAO. Elongated intact capillaries were identified in the siRNA-treated rats. Scale bar: 50 μm. The number of capillaries was increased by two-fold with the siRNA treatment. # P<0.0001; n=7. (C) TTC staining of the rat brains 1 day post MCAO. There was a significant reduction of infarct volume by siRNA treatment. **P<0.01; n=5.

Western blot analysis revealed that in the saline-treated animals, there was an upregulation of TRPM4 in the ipsilateral region and very low expression of TRPM4 in the contralateral region. Knockdown of TRPM4 via siRNA successfully prevented the upregulation of TRPM4 in the ipsilateral hemisphere 1 day post MCAO (FIG. 10A). TRPM4 protein levels were reduced to a level similar to that in the contralateral region. De novo expression of TRPM4 was previously shown to contribute to the damage of capillary integrity following SCI [Gerzanich V, et al., *Nat Med*, 15, 185-91 (2009)]. The capillary structure was studied in the rat brains 3 days post MCAO. In the saline-treated animals, the capillaries were generally short, and fragmentation was present in almost all capillaries (FIG. 10B). The capillaries within the penumbra region of the siRNA-treated animals were elongated without segmentation, indicating greater structural integrity. In addition, the number of capillaries in the penumbra region was increased 2.5-fold relative to the saline-treated animals (saline 8.8±0.8 vs. siRNA 21.4±0.5, P<0.0001, Student's t test). Thus, TRPM4 inhibition can promote angiogenesis in a rat model of stroke.

Next, it was examined whether TRPM4 deletion affects brain tissue loss after stroke. In the saline-treated animals 1 day post MCAO, large infarction was observed in the ipsilateral hemisphere according to TTC staining (FIG. 10C). Both the cortex and striatum were affected. By contrast, siRNA treatment greatly reduced infarction. The cortex was preserved almost completely, while a smaller infarction occurred mainly in the striatum. The infarction volume was greatly reduced from 24±32% to 8.8±1% (P=0.0017, Student's t test) (FIG. 10C).

Figure 11:
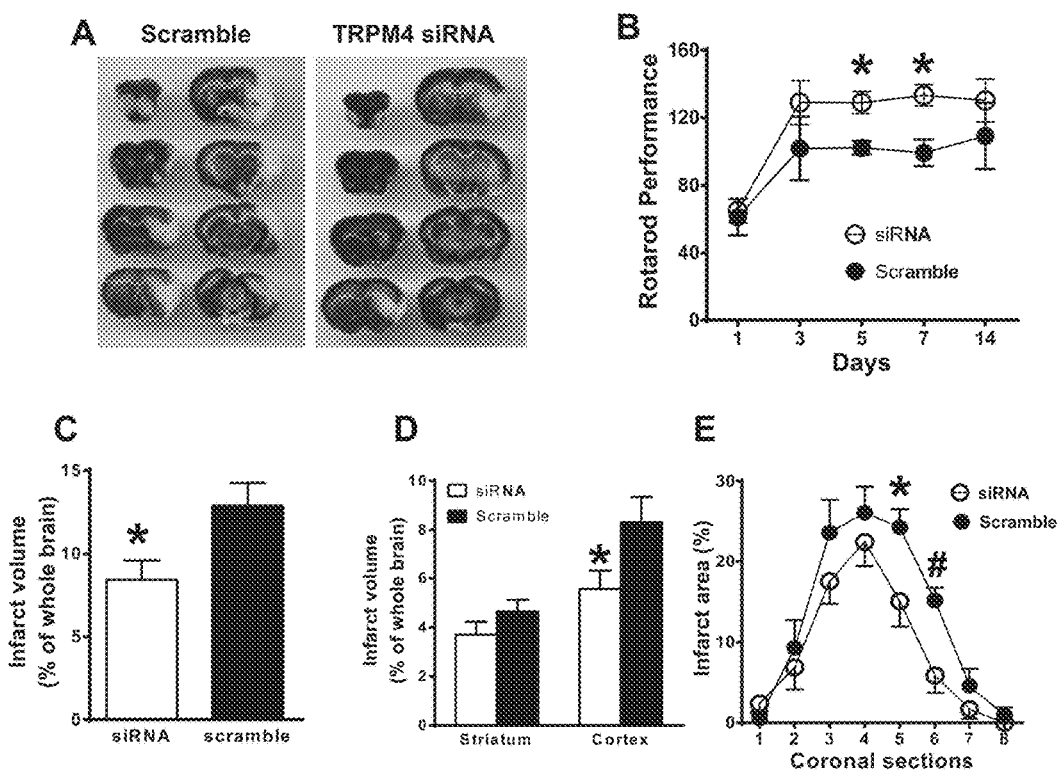
FIG. 11: TRPM4 inhibition reduces infarction and improves motor function in a transient rat stroke model. (A) TTC staining of the rat brains 24 hours after a two-hour MCAO. siRNA against TRPM4 reduces infarction. (B). Motor functions measured by rotarod indicate an enhanced functional recovery by TRPM4 inhibition. (C). Calculation of infarct volume reveals a reduction of overall infarct volume by siRNA treatment against TRPM4. (D). Infarct reduction is more prominent at the cortex region. (E). Infarct is significantly reduced at the $5^{th}$ and $6^{th}$ of coronal sections.
Figure 12:
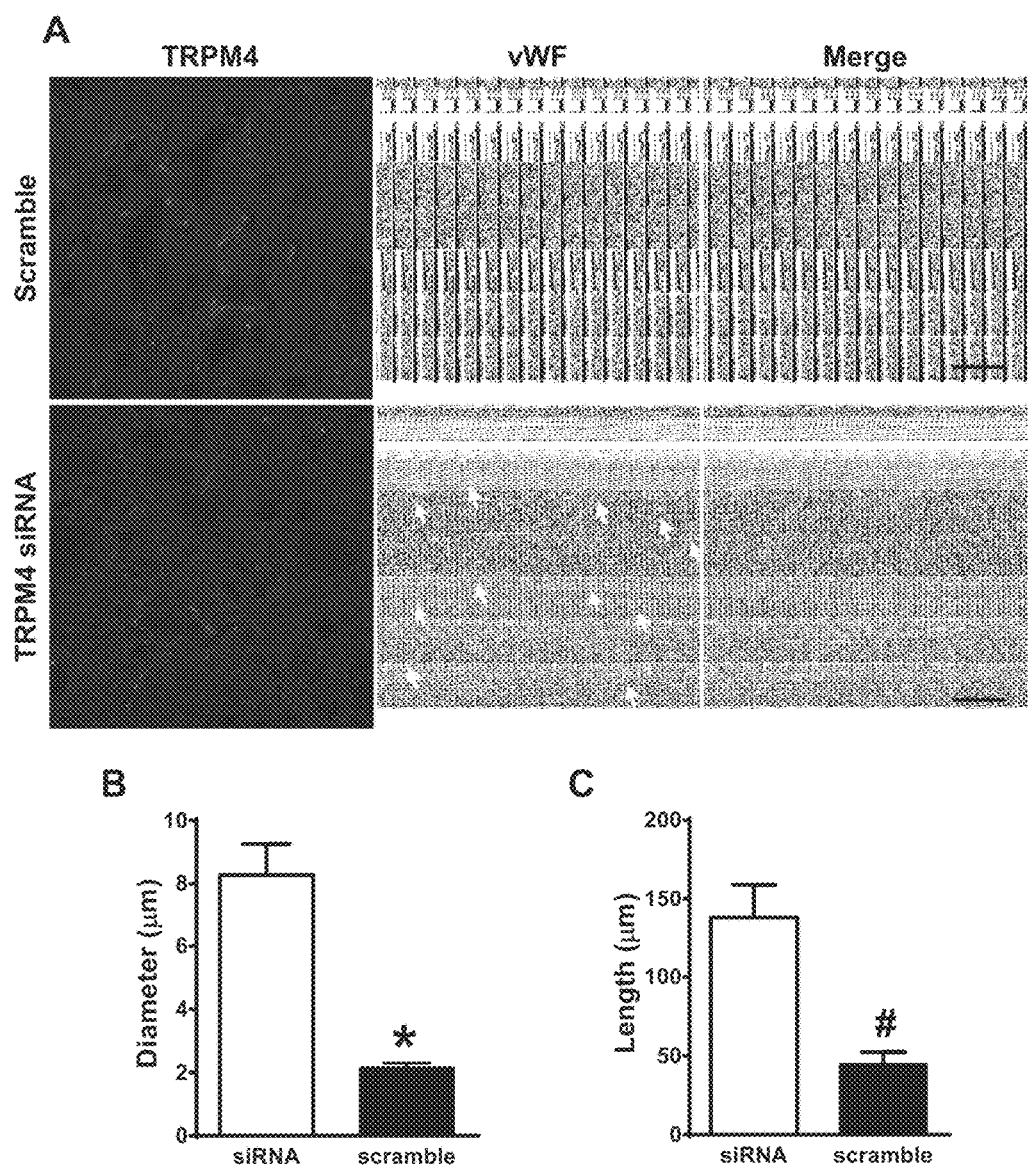
FIG. 12: TRPM4 siRNA treatment successfully down-regulated TRPM4 expression in a transient stroke model and improved angiogenesis. (A) Immunostaining of TRPM4 in vascular endothelium within the penumbra region in the rat brains following 2 hours MCAO. In scramble siRNA treated animals, TRPM4 colocalizes with vWF, a marker for endothelium, whereas in siRNA treated animals, TRPM4 expression is weakened in most capillaries. Scale bar 50 nm. The measurement of vascular diameter (B) and length (C) indicates pro-angiogenesis effect of siRNA. *p<0.0001; # p=0.0003.

Utilising the transient MCAO model also indicated that TRPM4 inhibition by siRNA is beneficial for reducing infarction volume and improving functional recovery (FIG. 11). Moreover, siRNA treatment enhances angiogenesis, as seen by significantly increased diameters and lengths of cerebral blood vessels compared to treatment with scrambled siRNA treatment (FIG. 12).

In Vivo TRPM4 Knockdown Improves Motor Function after MCAO

Figure 13:
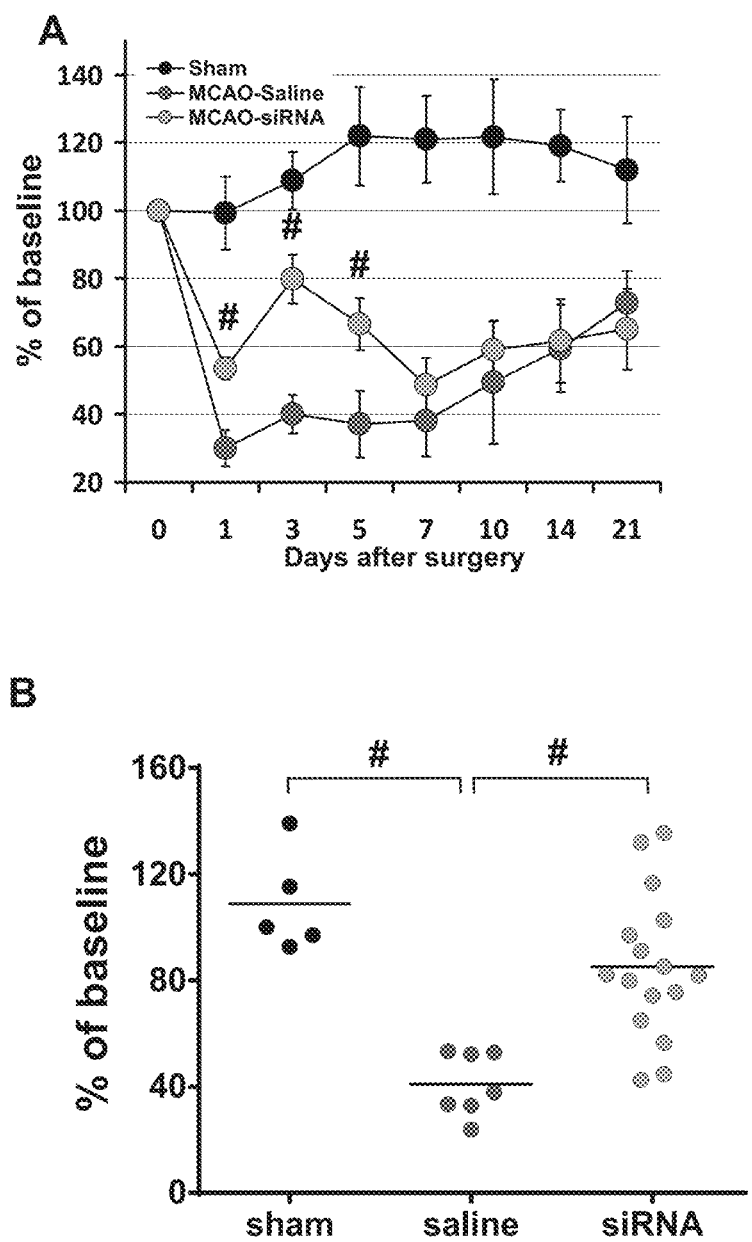
FIG. 13: TRPM4 knockdown via siRNA improves motor function during the acute phase of stroke. (A) Rotarod performance of the sham-operated, saline-treated, and TRPM4-siRNA treated MCAO rats. The data represent the percentage of the mean duration from 3 trials at each time point after normalization to the baseline control prior to the operation. The performance of the siRNA-treated rats was better than that of the saline-treated rats at days 1, 3, and 5. siRNA vs saline: # P<0.0001; $n_{sham}$=5; $n_{saline}$=6-7; $n_{siRNA}$=18-21. (B) Rotarod performance at day 3 post MCAO. Both sham-operated and siRNA-treated rats performed better than the saline-treated rats. # p<0.0001. There was no difference between the sham-operated and siRNA-treated animals.

A rotarod test was used to evaluate the motor function of the rats receiving siRNA treatment. The sham-operated animals performed well on the test (FIG. 13A). The performance of MCAO rats (n=8) receiving saline treatment decreased to 28±4% 1 day post operation and gradually improved in subsequent days. The performance of the 21 siRNA-treated MCAO rats greatly improved to 57±3.7% 1 day post MCAO, which is significantly higher than the saline group but lower than the sham-operated group (P<0.0001, one-way ANOVA followed by Dunnett's post hoc analysis). The effects of siRNA were most prominent 3 days post MCAO. There was no difference between the siRNA-treated animals and sham-operated animals (FIG. 13B). The protective effect lasted until day 5 post operation. By day 7, the motor function deficit in the siRNA-treated animals decreased to levels that were similar to those in the saline-treated animals (FIG. 13A).

Transient Protective Effect of TRPM4 Knockdown

Figure 14:
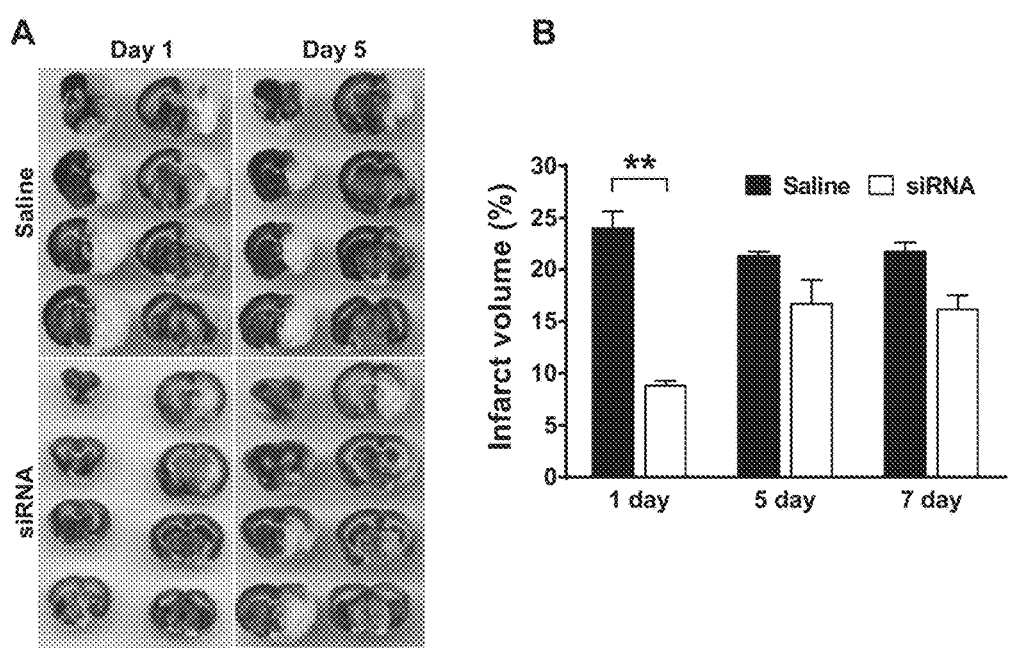
FIG. 14: Transient effect of TRPM4-siRNA treatment post stroke. (A) TTC-staining at day 1 and day 5 after MCAO. (B) Infarct volume measurement at day 1, 5, and 7 after MCAO. **P<0.01; n=5.

The results from the rotarod test suggest that TRPM4 knockdown does not maintain functional improvement after the acute phase of stroke. To study the effects of TRPM4 knockdown on tissue loss after the acute phase, TTC staining was performed to measure the infarction volume at different time points (FIG. 14A). In the saline-treated rats, the infarct volume decreased gradually by day 7, indicating that the process of reabsorption was occurring. By contrast, the protective effects of siRNA treatment disappeared by day 5. Although the mean infarct volumes were smaller than those in the saline-treated animals, there was no difference between the two groups (FIG. 14B). Thus, the protective effect of TRPM4 knockdown appears to be transient and occurs during the acute phase of stroke. These results support that brain tissue loss correlates with functional changes after MCAO.

Antibody Binds to TRPM4 Channel in Live Cells and Reduces Cell Death after OGD

Figure 15:
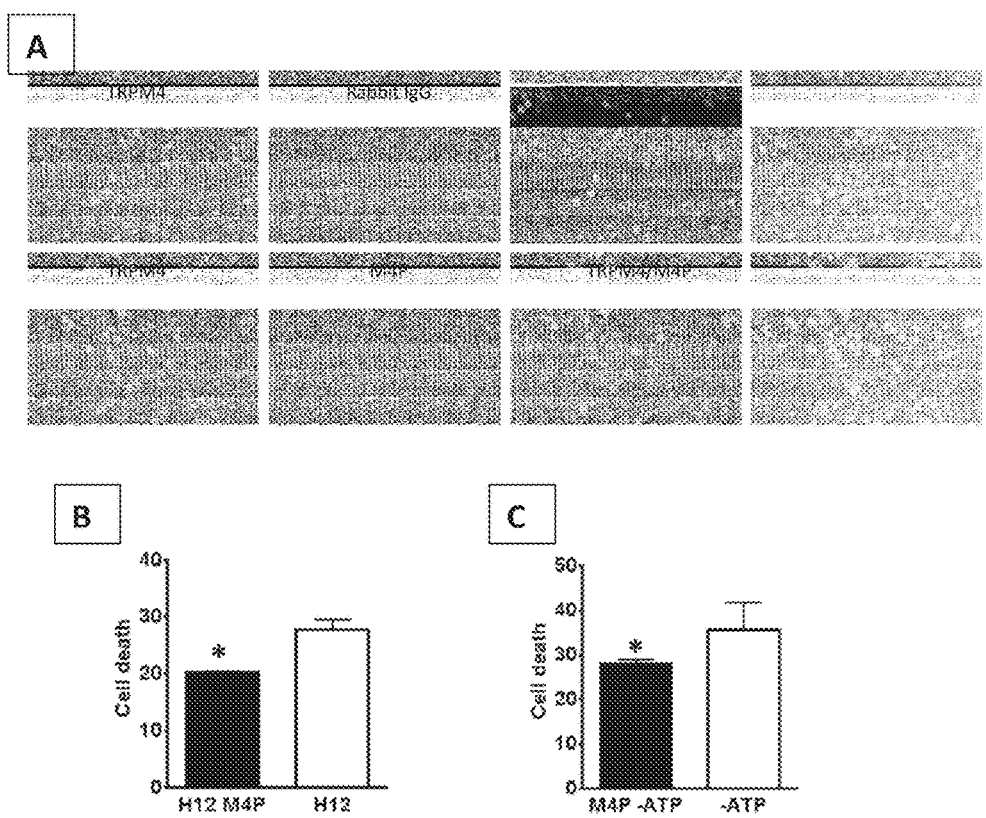
FIG. 15: Blocking TRPM4 with antibody reduced OGD induced cell death. (A) In HEK cells transfected with TRPM4 (green), M4P antibody (red) bind to the TRPM4 channels on the surface of live cells. Control antibody from rabbit IgG did not bind to the membrane TRPM4 channels. (B) M4P treatment significantly reduced hypoxia (12 hours incubation) induced cell death in HEK cells transfected with TRPM4. C M4P treatment significantly reduced chemicals (Sodium Azide and 2-Deoxy-D-glucose) induced cell death in HEK cells transfected with TRPM4. **P<0.05.

As no potent TRPM4 blockers can be used in vivo, an antibody was developed against TRPM4 that could potentially block the channel. After targeting various extracellular regions of TRPM4, one antibody M4P was able to bind to the TRPM4 channels in vivo (FIG. 15A). Incubation with M4P in live HEK cells transfected with TRPM4 showed a strong membrane localization, which was absent in control rabbit IgG treatment. To test the therapeutic effect, TRPM4 transfected HEK cells were incubated in hypoxic gas and in medium without glucose. Cell death was greatly reduced with M4P treatment after. 12 hour OGD (FIG. 15B). In chemicals treated cells (Sodium Azide and 2-Deoxy-D-glucose), M4P yielded similar protective effect (FIG. 15C).

Figure 16:
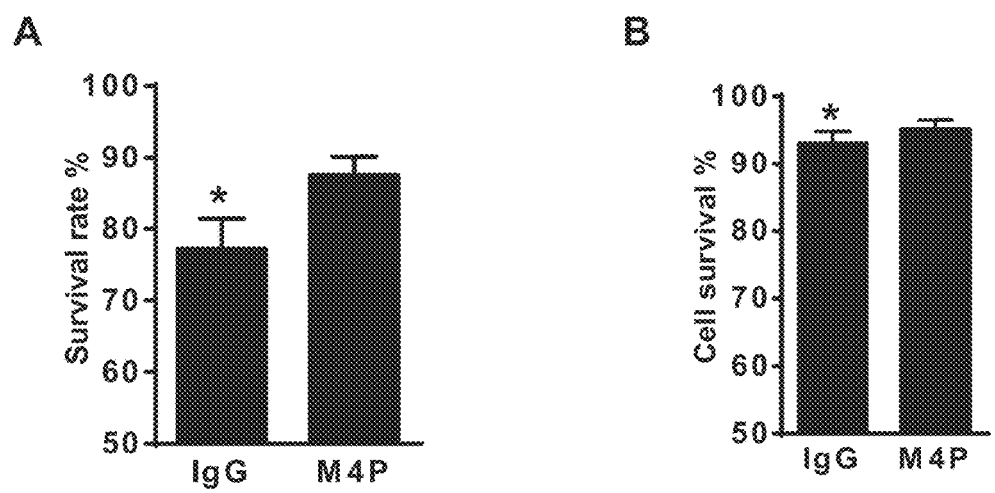
FIG. 16: Under oxygen glucose deprivation (OGD) for 24 hours, M4P treatment increases cell survival both in HEK cells transfected with mouse TRPM4 (A) and in human cerebral vascular endothelial cells (B).

After 24 hours OGD M4P treatment increased cell survival both in HEK cells (FIG. 16A) and in human cerebral vascular endothelial cells (FIG. 10B). Although rats and humans share 61% identity in the epitope recognized by M4P, the M4P antibody successfully protected the human cerebral vascular endothelial cells from hypoxia.

The antibody directed to the intracellular region (SEQ ID NO: 4) of TRPM4 did not effectively bind to the TRPM4 channel in both transfected cells and human brain endothelial cells (data not shown).

A review of the progress of the development of therapeutic antibodies for stroke [Yu C Y, et al., *Transl Stroke Res* 4(5): 477-83 (2013)], suggests very few channels have been targeted. Antibodies against the NMDA receptor have been extensively studied, however, severe side effects led to the termination of clinical trials. As the NMDA receptor is ubiquitously expressed in the brain, blocking NMDA receptor after stroke could affect neurons within the healthy brain tissue and cause unwanted side effects. In contrast to the NMDA receptor, TRPM4 may be an ideal target as it is not abundantly expressed in healthy brain tissue and are therefore less likely to be affected by TRPM4 blockers. TRPM4 knockout mice appear healthy with no major deficits [Vennekens R, et al., *Nat Immunol* 8(3): 312-20 (2007a)] indicating that the side effects of blocking TRPM4 in other organs and tissues could be minimal during the time for stroke treatment. As a polyclonal antibody, M4P cannot be used directly in human patients. Therefore, a humanized antibody directed to the same region of TRPM4 that the M4P antibody binds to would be useful for treatment in human patients.

Figure 17:
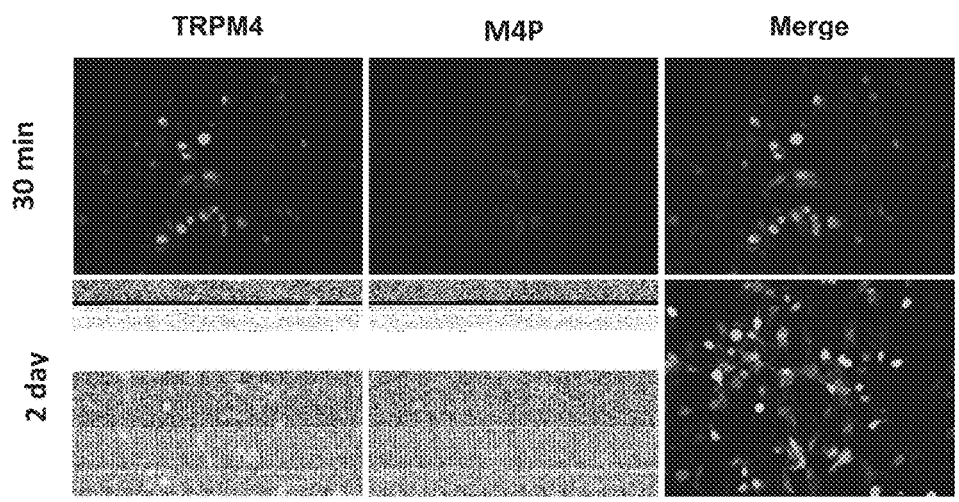
FIG. 17: In HEK cells transfected with mouse TRPM4, M4P is able to bind to the surface of the live HEK cells after 30 min incubation (upper row). After prolonged incubation for 2 days, M4P is internalized into cytosol of HEK cells (lower row). Therefore, M4P likely to inhibit TRPM4 in two mechanisms: by blocking TRPM4 channel in the acute stage and by downregulate surface TRPM4 expression via internalizing membrane TRPM4 protein in the chronic stage.

Antibody Binds to TRPM4 in Live Cells and is Internalized Under Prolonged Incubation The in vitro study shows that antibody M4P could bind to the membrane TRPM4 channels after incubation for only 30 minutes and, under prolonged incubation, TRPM4 channels on the cell membrane can be internalized by M4P into the cytoplasm (FIG. 17).

Antibody Binds to TRPM4 Transfected HEK Cells and Inhibits Channel Currents.

Figure 18:
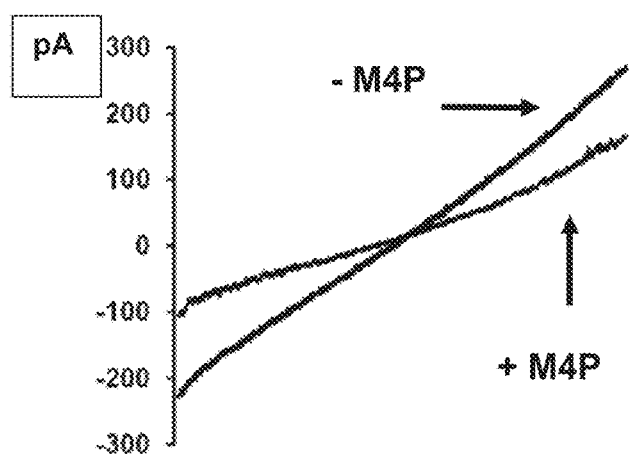
FIG. 18: M4P antibody at 60 μg/ml concentration is able to reduce the currents from mouse TRPM4 channels expressed in I ICK cells.

Voltage clamp recordings showed that binding of antibody M4P to cells transfected with the rat TRPM4 channel inhibited whole-cell currents (FIG. 18).

Therefore, antibodies directed to the same epitope as M4P are likely to inhibit TRPM4 in two mechanisms: by blocking TRPM4 channel in the acute stage and by downregulating surface TRPM4 expression via internalizing membrane TRPM4 protein in the chronic stage.

Discussion

The ectopic expression and activation of TRPM4 is generally harmful to cells. Under pathological conditions, an increase in intracellular $Ca^{2+}$ concentrations and the depletion of ATP leads to TRPM4 activation [Vennekens R, Nilius B., *Handb Exp Pharmacol*, 269-85 (2007b)], resulting in oncotic cell death due to unchecked $Na^+$ influx [Gerzanich V, et al., *Nat Med*, 15, 185-91 (2009)]. The cessation of the blood supply to part of the brain after ischemic stroke can increase intracellular $Ca^{2+}$ levels and lower ATP concentrations within the affected area; both of these events can enhance TRPM4 activities.

In the central nervous system, de novo expression of TRPM4 has also been identified in the capillaries, following SCI [Gerzanich V, et al., *Nat Med*, 15, 185-91 (2009)]. In the present study a similar upregulation of TRPM4 protein was observed in the capillary endothelia after stroke. In cultured HUVECs, TRPM4 was expressed at basal levels under normoxic conditions, similar to a previous report [Becerra A, et al., *Cardiovasc Res*, 91, 677-84 (2011)]. In this study, TRPM4 expression is low in the healthy rat brain. The culture conditions may have caused the increased TRPM4 expression in HUVECs. OGD treatment increased TRPM4 expression at both the transcriptional and translational levels. Blocking TRPM4 channels with 9-phenanthrol enhanced tube formation, a sign of angiogenesis after hypoxia. Thus, the upregulation of TRPM4 is harmful to endothelial cells, and TRPM4 inhibition can protect HUVECs from hypoxic insult. This is supported by another study indicating that blocking TRPM4 can prevent HUVECs from lipopolysaccharide-induced cell death [Becerra A, at al., *Cardiovasc Res*, 91, 677-84 (20111]

In SCI, de novo expression of TRPM4 in the endothelium caused capillary fragmentation, and deletion of TRPM4 greatly enhanced recovery by promoting angiogenesis [Gerzanich V, et al., *Nat Med*, 15, 185-91 (2009)]. The loss of vascular integrity was also apparent within the penumbra region using MCAO model in this study. TRPM4 knockdown via siRNA greatly promoted angiogenesis and improved the motor functions of the rats. This indicates that the upregulation of TRPM4 in the endothelium following stroke plays a similar pathological role as in traumatic SCI. The increased expression of TRPM4 in the capillaries after SCI led to secondary hemorrhage. It is possible that the upregulation of TRPM4 is a cause of hemorrhage transformation observed in many patients with ischemic stroke.

In the MCAO model, the animals that were treated with the siRNA displayed not only intact capillaries but also an increased number of capillaries compared to the saline-treated rats. However, blocking TRPM4 in HUVECs only improved tube formation without increasing the cell number. This could be due to the differences in the levels of growth factors in the two studies. In the animal model, VEGF and other growth factors generated after the onset of stroke could promote capillary proliferation, whereas in HUVECs under OGD, the serum and growth factors were completely removed. Thus, no cell proliferation was observed.

The ectopic expression of TRPM4 within the axonal processes contributes to the tissue damage induced by EAE [Schattling B, et al., *Nat Med*, 18, 1805-11 (2012)]. TRPM4 was also found in cerebral vascular smooth muscle cells. Blocking TRPM4 with antisense oligonucleotides greatly reduced pial artery constriction [Reading S A, Brayden J E, *Stroke*, 38, 2322-8 (2007)]. More experiments are needed to clarify the role of TRPM4 in neurons and vascular smooth muscles after stroke.

The expression of TRPM4 was transient after ischemic stroke. It peaked within 1 day and then gradually decreased. As angiogenesis occurs soon after the onset of stroke, TRPM4 is likely to affect the regeneration of capillaries. In fact, TRPM4 knockdown immediately after MCAO preserved vascular integrity, enhanced angiogenesis, and as a result, reduced infarction, and promoted functional recovery. However, the effect of siRNA treatment was transient. By day 5, the rotarod performances of the animals were similar to those of the saline-treated rats. These results suggest that TRPM4 upreguiation only participates in endothelial damage during the acute phase of stroke. This is supported by the observation that by day 7, many vascular endothelial cells did not express TRPM4 channels; The mechanism for this unique expression pattern is not known. Acute stroke reperfusion treatments are currently restricted by the very narrow time window (<4.5 hours for intravenous thrombolysis), limiting this treatment to only a minority of patients. This is due to the progression of the ischemic penumbra to infarction over the first few hours following cerebral arterial occlusion [Astrup J, et al., *Stroke*, 12, 723-5 (1981)]. According to the animal data in the present study, blocking TRPM4 during the acute phase protects the brain tissue for as long as 5 days, Thus, blocking TRPM4 could potentially extend the therapeutic time window of acute reperfusion treatments.

Currently, there are no safe and specific TRPM4 blockers that can be used In vivo. A polyclonal antibody was developed, namely M4P, which can bind to and block TRPM4 channels. The data shows that M4P can bind to live cells expressing TRPM4 channels on the membrane surface. In cultured cells, M4P treatment significantly reduced hypoxia induced cell death and inhibited TRPM4 channel currents. In general, antibodies are large molecules and have difficulties in passing through the blood-brain barrier (BBB). However, the BBB integrity is compromised after stroke. Thus, antibodies can enter the brain areas that are affected by stroke. Furthermore, the main target of the M4P antibody is the endothelial TRPM4. It is easier for the antibody to bind to the TRPM4 channels on the capillaries. From the functional study, blocking TRPM4 during acute phase of stroke could extend the tissue loss to a later time point. Currently, the narrow time window of reperfusion therapy limits this therapy only to a small number of stroke patients. Blocking TRPM4 with antibodies could extend the time window and benefit more stroke patients.

In summary, the transient expression of TRPM4 during the acute phase following ischemic stroke is critical for capillary integrity. Blocking TRPM4 can protect brain tissue by promoting angiogenesis and represents a potential drug target for stroke therapy during both the acute and chronic stages.

As used herein, the term 'comprising' does not preclude the presence of additional steps or substances in the methods and compositions, respectively, of the invention, and is understood to include within its scope the more restrictive terms 'consisting of' and 'consisting essentially of' features defined in the claimed invention.

REFERENCES

1. Astrup J, et al., (1981) *Stroke,* 12: 723-5.
2. Becerra A, et al., (2011) *Cardiovasc Res,* 91: 677-84.
3. Chandrashekran A, et al., (1983) *Hybridoma* 2(4): 451-7.
4. Cianfriglia M, et al., (1983) *Hybridoma;* 2(4): 451-7.
5. Cole et al., in *Monoclonal Antibodies and Cancer Therapy* (Vol. 27, UCLA Symposia on Molecular and Cellular Biology, New Series) (eds. R. A. Reisfeld and S. Sell), pp. 77-96, Alan R. Liss, Inc. N.Y., (1985).
6. De Meyer S F, et al., (2012) *Stroke,* 43: 599-606.
7. Favilla C G, et al., (2011) *Stroke* 42: 710-5.
8. Gerzanich V, et al., (2009) *Nat Med,* 15: 185-91.
9. Grand T, et al., (2008) *Br J Pharmacol,* 153: 1697-705.
10. Hammerling et al., eds. *Monoclonal Antibodies and T-cell Hybridomas: Perspectives and Technical Advances.* New York, N.Y.: Elsevier/North Holland; (1981).
11. Hood et al., in *Immunology,* p. 384, Second Ed., Benjamin/Cummings, Menlo Park, Calif., (1984).
12. Kahle K T, et al., (2009) *Physiology* (Bethesda), 24: 257-65.
13. Karagiannis P, et al., (2009) *Cancer Immunol Immunother* 58: 915-30.
14. Kohler et al., (1975) *Nature,* 256: 495-497.
15. Kozbor et al., (1983) *Immunology Today,* 4: 72.
16. Kruse M, et al., (2009) *J Clin Invest,* 119: 2737-44.
17. Kunte H, et al., (2012) *Ann Neurol* 72: 799-806.
18. 21. Liao P, et al., (2004) *J Biol Chem,* 279: 50329-35.
19. Morrison, et al., (1984) *Proc Natl Acad Sci USA,* 81: 6851-6855.
20. Neuberger, et al., (1984) *Nature* 312: 604-608.
21. Nilius B, et al., (2003) *J Biol Chem,* 278: 30813-20.
22. Nilius B, et al., (2005) *J Biol Chem.* 280(24): 22899-906.
23. Nilius B, et al., (2007) *Physiol Rev,* 87: 165-217.
24. Reading. S A, Brayden J E. (2007) *Stroke,* 38: 2322-8.
25. Riechmann L, et al., (1988) *Nature* 332(6162): 323-7.
26. Sala-Rabanal M, et al., (2012) *J Biol Chem* 287: 8746-56.
27. Sambrook and Russell, Molecular Cloning: A Laboratory Manual, Cold Springs Harbor Laboratory, New York (2001).
28. Schattling B, et al., (2012) *Nat Med,* 18. 1805-11.
29. Simard J M, et al.; (2006) *Nat Med,* 12: 433-40.
30. Simard J M, et al, (2010) *J Neurosurg.* 113: 622-9.
31. Takeda, et al., (1985) *Nature,* 314: 452-454.
32. Vennekens R, et al., (2007a) *Nat Immunol,* 8: 312-20.
33. Vennekens R, Nilius B. (2007b) *Handb Exp Pharmacol,* 269-85.
34. Verhoeyen M, et al., (1988) *Science. March 25;* 239 (4847): 1534-6.
35. Walcott B P, et al., (2012) *Neurotherapeutics* 9: 65-72.
36. Woo S K, et al., (2012) *J Biol Chem M*112.428219 [pii] 10.1074/jbc.M112.428219.
37. Yu C Y, et al., (2013) *Transl Stroke Res.* 4(5): 477-83.
38. Zhao. H, et al., (2005) *J Neurosci,* 25: 9794-806.

The invention claimed is:

1. An isolated antibody specific to the transient receptor potential melastatin 4 (TRPM4) protein, wherein:
    the antibody specifically binds to a peptide consisting of the amino acid sequence of SEQ ID NO: 1, a peptide consisting of the amino acid sequence of SEQ ID NO: 2, or a peptide consisting of the amino acid sequence of SEQ ID NO: 3,
    the antibody specifically binds to an epitope comprising amino acids 949-952 and 985-1008 of SEQ ID NO: 11 or amino acids 955-958 and 991-1014 SEQ ID NO: 12, and
    the antibody inhibits TRPM4 activity.

2. The antibody according to claim 1, wherein the antibody is a polyclonal, monoclonal or humanized antibody.

3. The antibody according to claim 1, wherein the antibody is a mouse-human chimeric antibody.

4. The antibody according to claim 1, wherein said antibody inhibits TRPM4 currents.

5. A kit for treating stroke, the kit comprising at least one antibody according to claim 1 and, optionally, at least one thrombolytic agent.

6. The antibody according to claim 1, wherein the antibody specifically binds to an epitope comprising amino acids 955-958 and 991-1014 SEQ ID NO: 12.

* * * * *